(12) United States Patent
Scott et al.

(10) Patent No.: US 12,402,880 B1
(45) Date of Patent: Sep. 2, 2025

(54) DUMMY CARTRIDGE WITH LOAD CELLS FOR MEASURING TISSUE THICKNESS AND INDICATING CARTRIDGE SELECTION

(71) Applicant: Cilag GmbH International, Zug (CH)

(72) Inventors: Gregory Scott, Fort Collins, CO (US); Bradley A. Arnold, Mason, OH (US); Mallory Schroeder, San Jose, CA (US); Ryan Reese, Cincinnati, OH (US); Shane Adams, Lebanon, OH (US); Marissa Talia Kamenir, Cincinnati, OH (US); Carolyn Williams, Cincinnati, OH (US); Patrick M Schleitweiler, West Chester, OH (US); Dhruv Patel, Hudson, OH (US); Nicholas William Seipelt, Milford, OH (US); Karen Averbeck, Dayton, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/634,429

(22) Filed: Apr. 12, 2024

(51) Int. Cl.
*A61B 17/072* (2006.01)
*A61B 17/00* (2006.01)
*A61B 90/00* (2016.01)

(52) U.S. Cl.
CPC ... *A61B 17/072* (2013.01); *A61B 2017/00115* (2013.01); *A61B 2017/07257* (2013.01); *A61B 2017/07271* (2013.01); *A61B 2017/07278* (2013.01); *A61B 2090/064* (2016.02); *A61B 2090/3908* (2016.02)

(58) Field of Classification Search
CPC .................................................. A61B 17/072
See application file for complete search history.

(56) References Cited

U.S. PATENT DOCUMENTS

| | | | |
|---|---|---|---|
| 8,210,411 | B2 | 7/2012 | Yates et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,724,094 | B2 * | 8/2017 | Baber ............... H02H 3/207 |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 10,092,292 | B2 | 10/2018 | Boudreaux et al. |
| 10,182,813 | B2 | 1/2019 | Leimbach et al. |
| 11,304,697 | B2 | 4/2022 | Fanelli et al. |

(Continued)

*Primary Examiner* — Nathaniel C Chukwurah
(74) *Attorney, Agent, or Firm* — Lempia Summerfield Katz LLC

(57) ABSTRACT

An end effector of a surgical instrument may be equipped with a staple cartridge selection system, including a load sensing cartridge insertable into a channel of a cartridge jaw of an end effector for assembly therewith, the load sensing cartridge including: a body having a proximal end portion and a distal end portion; an elongated channel within the body between the proximal end portion and the distal end portion; a load sensor disposed within the elongated channel of the load sensing cartridge, the load sensor configured to sense a parameter indicative of a tissue thickness when tissue is clamped between an anvil jaw and the cartridge jaw in the clamped configuration; and a visual indicator configured to display a visual indication based on the parameter sensed by the load sensor.

20 Claims, 17 Drawing Sheets

(56) References Cited

U.S. PATENT DOCUMENTS

| | | |
|---|---|---|
| 11,317,912 B2 | 5/2022 | Jenkins et al. |
| 11,439,391 B2 | 9/2022 | Bruns et al. |
| 2011/0204119 A1* | 8/2011 | McCuen .............. A61B 17/068 |
| | | 227/175.1 |
| 2017/0296179 A1* | 10/2017 | Shelton, IV ........... G16H 20/40 |

* cited by examiner

DUMMY CARTRIDGE WITH LOAD CELLS FOR MEASURING TISSUE THICKNESS AND INDICATING CARTRIDGE SELECTION

BACKGROUND

Open surgery (e.g., traditional surgery, conventional surgery, open or non-endoscopic procedures, and the like) involves creating a single large incision in the body to access the affected area. During open surgery, a surgeon may work directly with their hands and may have a broader view of the surgical site. In some instances, such as in the case of transplants, large incisions are necessary to remove the damaged organ and replace it with a healthy one. This type of surgery is also used in a variety of treatments, such as the removal of kidney stones.

Surgical staplers are frequently used in surgical procedures for suturing body tissues such as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. During the typical suturing process, pusher members associated with the cartridge are controllably advanced by the operating mechanism of the instrument in a manner to urge the staples out of the cartridge, through the tissue and forcibly against the anvil.

One such frequently used type of surgical stapler is the open linear stapler, which is a device that enables the surgeon to simultaneously place one or more rows of surgical staples in body tissue or organs. By way of example, a typical procedure is a pneumectomy, which is a removal of a portion of the patient's lungs. The linear stapler can be used several times during this procedure, including for the occlusion of the pulmonary artery prior to its resection. For this later use, the surgeon first clamps the jaws of the stapler across the artery, then forms the staple and before reopening the stapler jaws, cuts the artery with a scalpel using the edge of the staple jaws as a guide.

In some settings, endoscopic or laparoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path.

Staple cartridge selection for endoscopic surgical staplers is currently done via visual estimation during surgery, despite staple cartridges being designed for very specific tissue thickness ranges. Additionally, in both marching and single transection procedures, the clinician may have a need to measure the tissue before firing, e.g., to make a proper staple cartridge selection to enhance surgical performance. However, known surgical staplers (both endoscopic and open surgical staplers) have limited capabilities for providing information to enable such selections.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
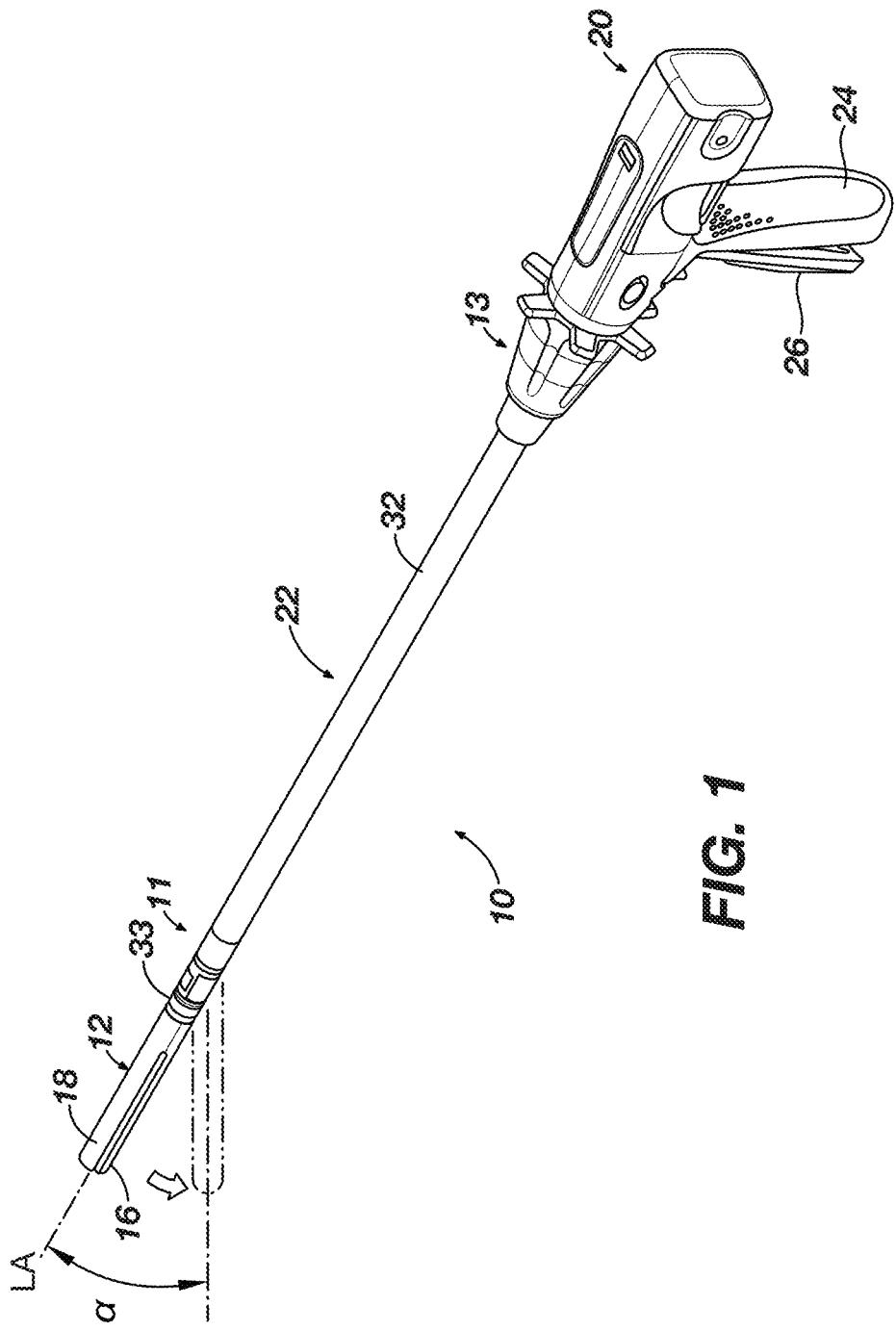
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Stapler

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected from the longitudinal axis (LA) of shaft 22 at a desired angle (a). End effector 12 of the present example includes a lower jaw 16 (also referred to herein as a cartridge jaw) that includes a staple cartridge 37, and an upper jaw in the form of a pivotable anvil jaw 18.

Unless otherwise described, the term "pivot" (and variations thereof) as used herein encompasses but is not necessarily limited to pivotal movement about a fixed axis. For instance, in some versions, anvil jaw 18 may pivot about an axis that is defined by a pin (or similar feature) that slidably translates along an elongated slot or channel as anvil jaw 18 moves toward lower jaw 16. Such translation may occur before, during, or after the pivotal motion. It should therefore be understood that such combinations of pivotal and translational movement are encompassed by the term "pivot" and variations thereof as used herein.

Handle portion 20 includes a pistol grip 24 and a closure trigger 26. Closure trigger 26 is pivotable toward pistol grip 24 to cause clamping, or closing, of anvil jaw 18 toward lower jaw 16 of end effector 12. Such closing of anvil jaw 18 is provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33.

Figure 2:
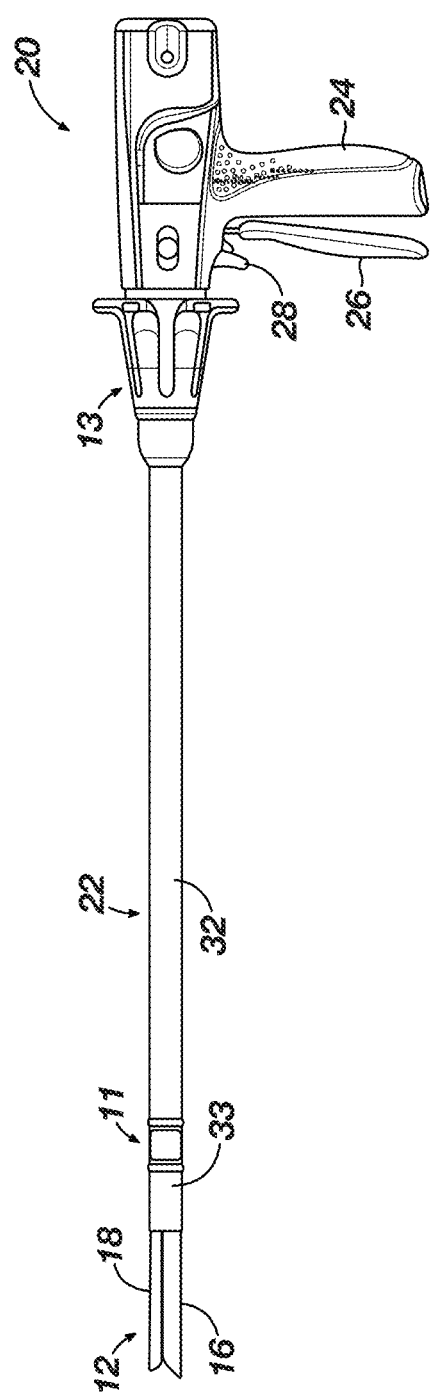
FIG. 2 depicts a side view of the instrument of FIG. 1.

As shown in FIG. 2, handle portion 20 also includes a firing trigger 28. An elongate member (not shown) longitudinally extends through shaft 22 and communicates a longitudinal firing motion from handle portion 20 to a firing beam 14 in response to actuation of firing trigger 28. This distal translation of firing beam 14 causes the stapling and severing of clamped tissue in end effector 12, as will be described in greater detail below.

As shown in FIGS. 3-6, end effector 12 employs a firing beam 14 that includes a transversely oriented upper pin 38, a firing beam cap 44, a transversely oriented middle pin 46, and a distally presented cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44.

Figure 3:
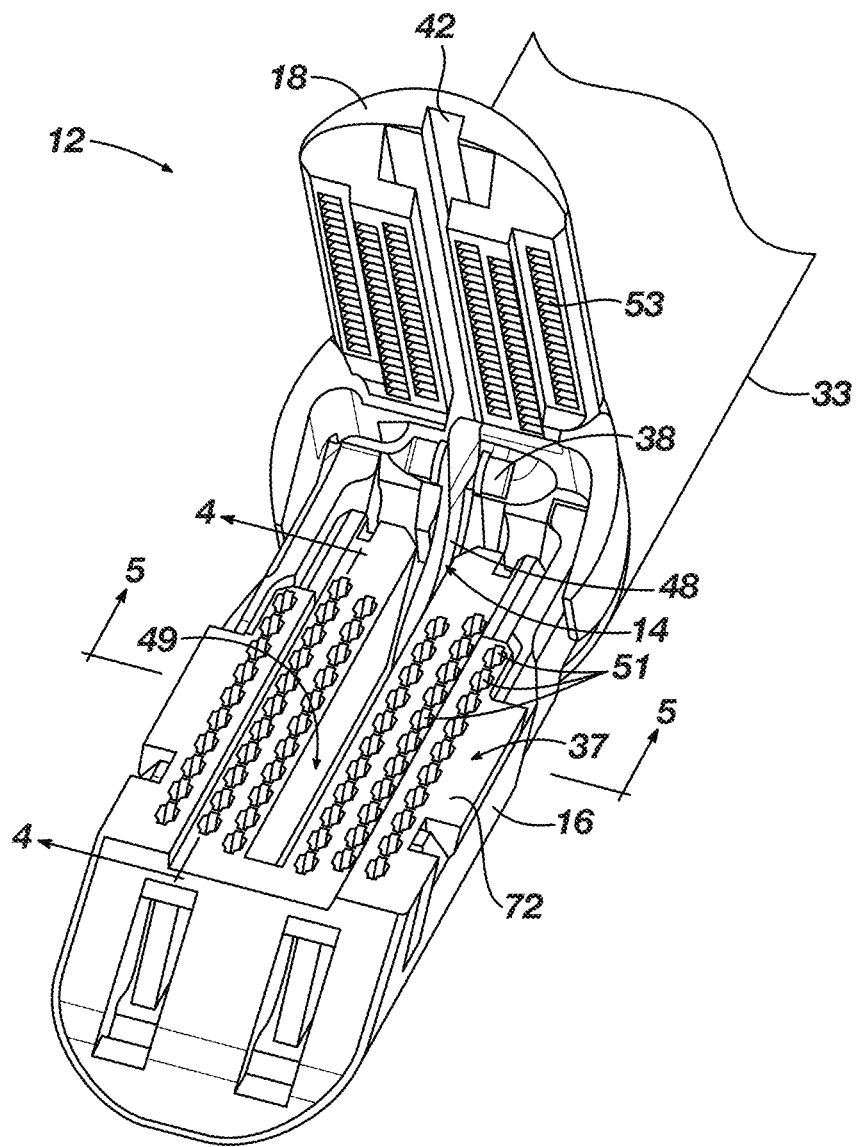
FIG. 3 depicts a perspective view of an opened end effector of the instrument of FIG. 1.
Figure 4A:
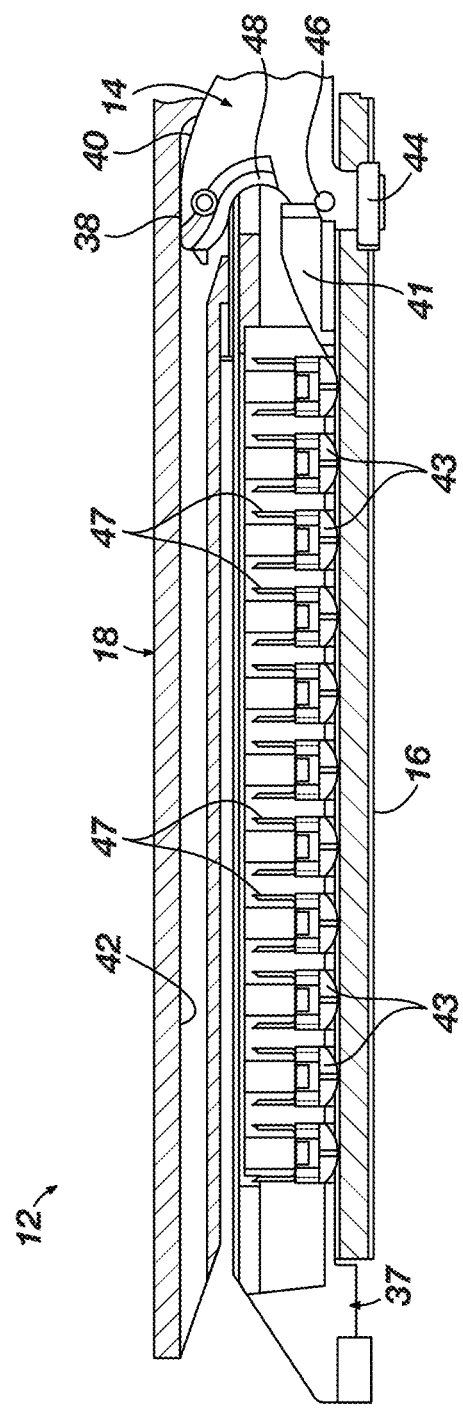
FIG. 4A depicts a side cross-sectional view of the end effector of FIG. 3, taken along line 4-4 of FIG. 3, with the firing beam in a proximal position.
Figure 4B:
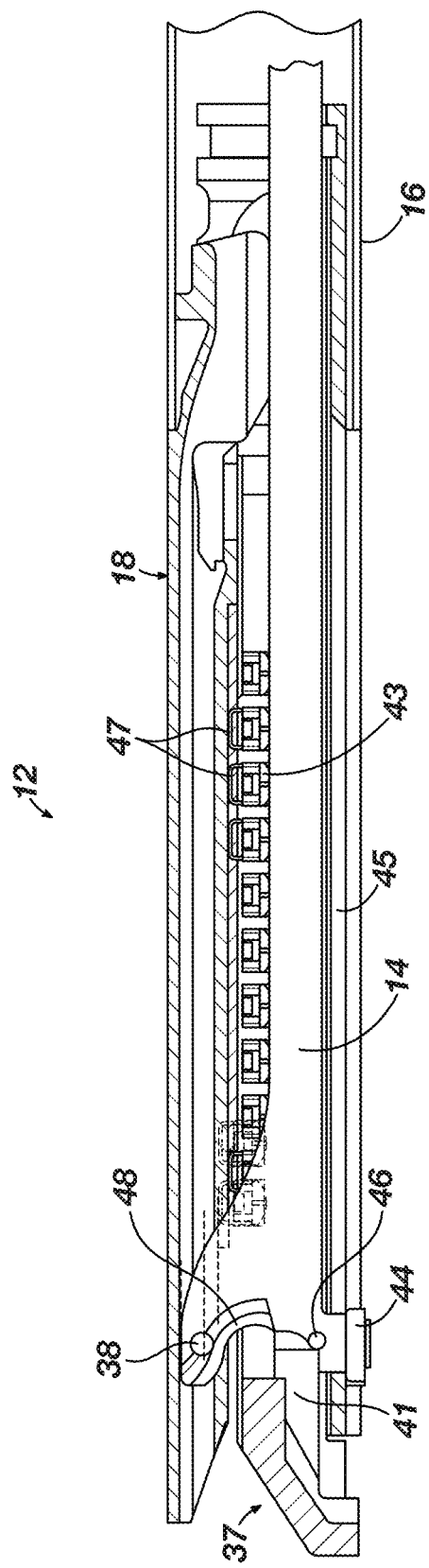
FIG. 4B depicts a side cross-sectional view of the end effector of FIG. 3, taken along line 4-4 of FIG. 3, with the firing beam in a distal position.
Figure 5:
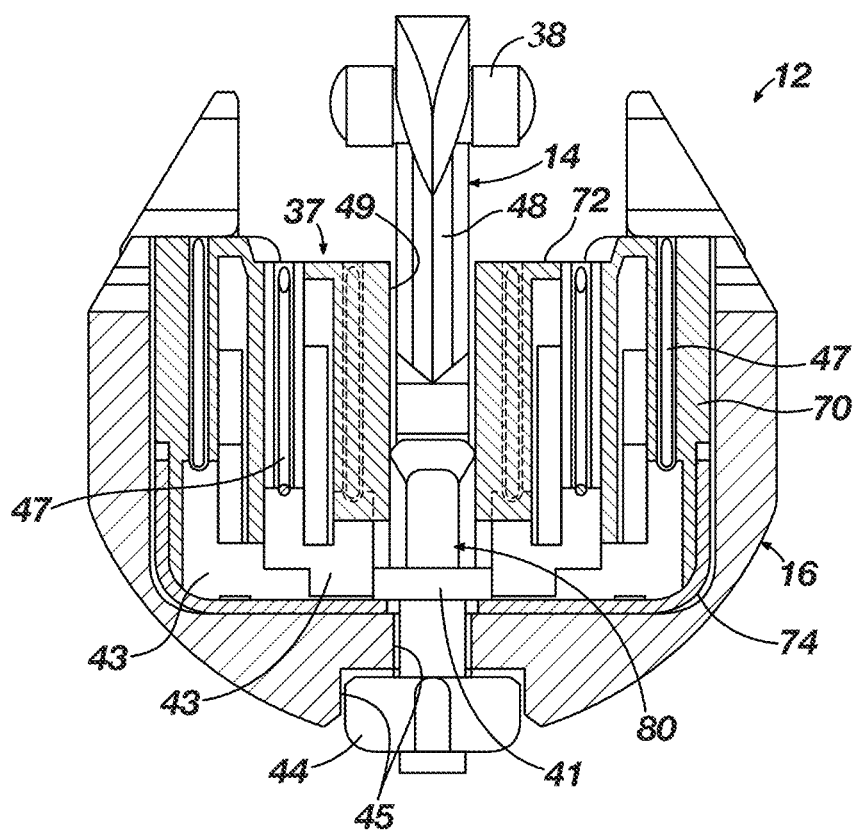
FIG. 5 depicts an end cross-sectional view of the end effector of FIG. 3, taken along line 5-5 of FIG. 3.
Figure 6:
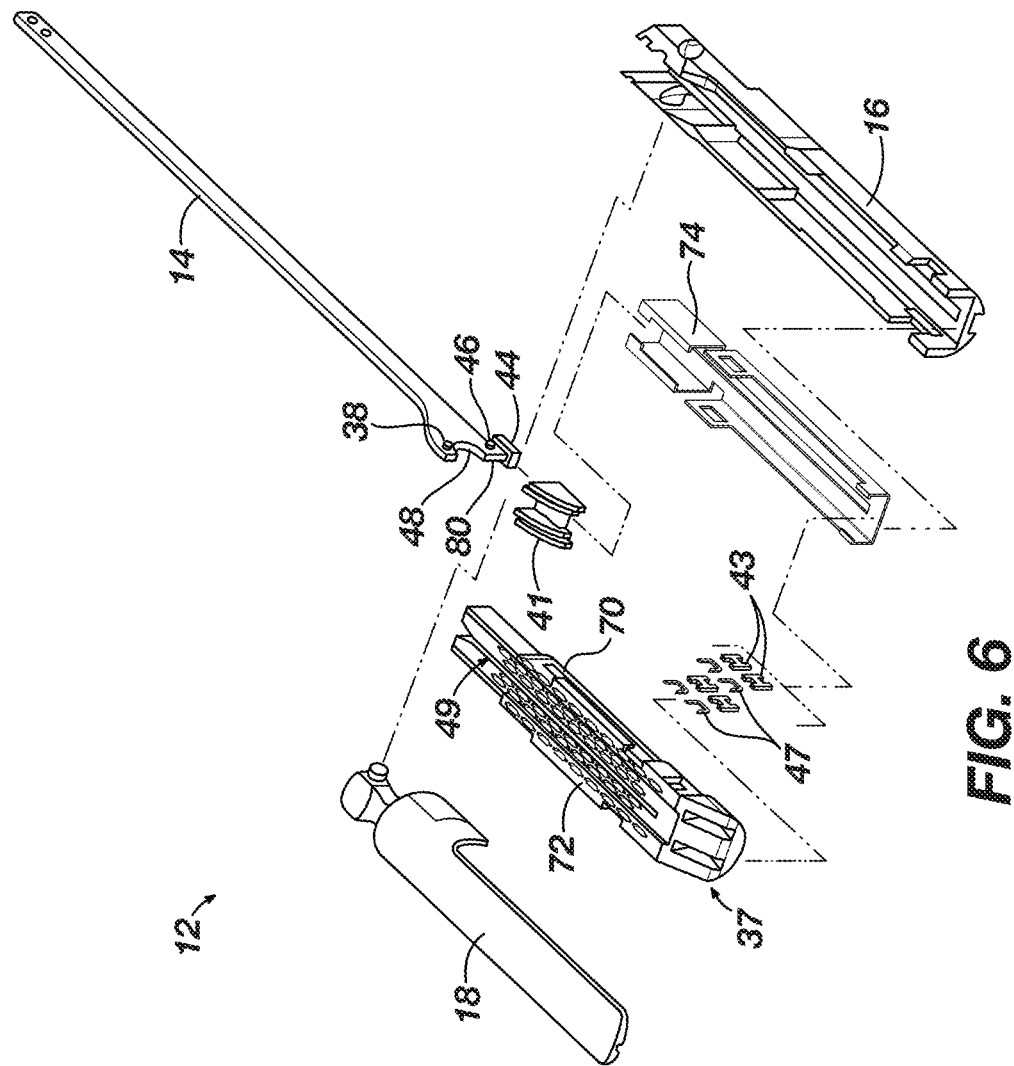
FIG. 6 depicts an exploded perspective view of the end effector of FIG. 3.

FIG. 3 shows firing beam 14 of the present example proximally positioned and anvil jaw 18 pivoted to an open configuration, allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80 (shown in FIG. 5) located at distal end of firing beam 14 pushes wedge sled 41 distally as firing beam 14 is advanced distally through staple cartridge 37 when firing trigger 28 is actuated. During such firing, cutting edge 48 of firing beam 14 enters vertical slot 49 of staple cartridge 37, severing tissue clamped between staple cartridge 37 and anvil jaw 18. As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS. 4A-4B but are shown in FIG. 3. Anvil jaw 18 is intentionally omitted from the view in FIG. 5.

Figure 7:
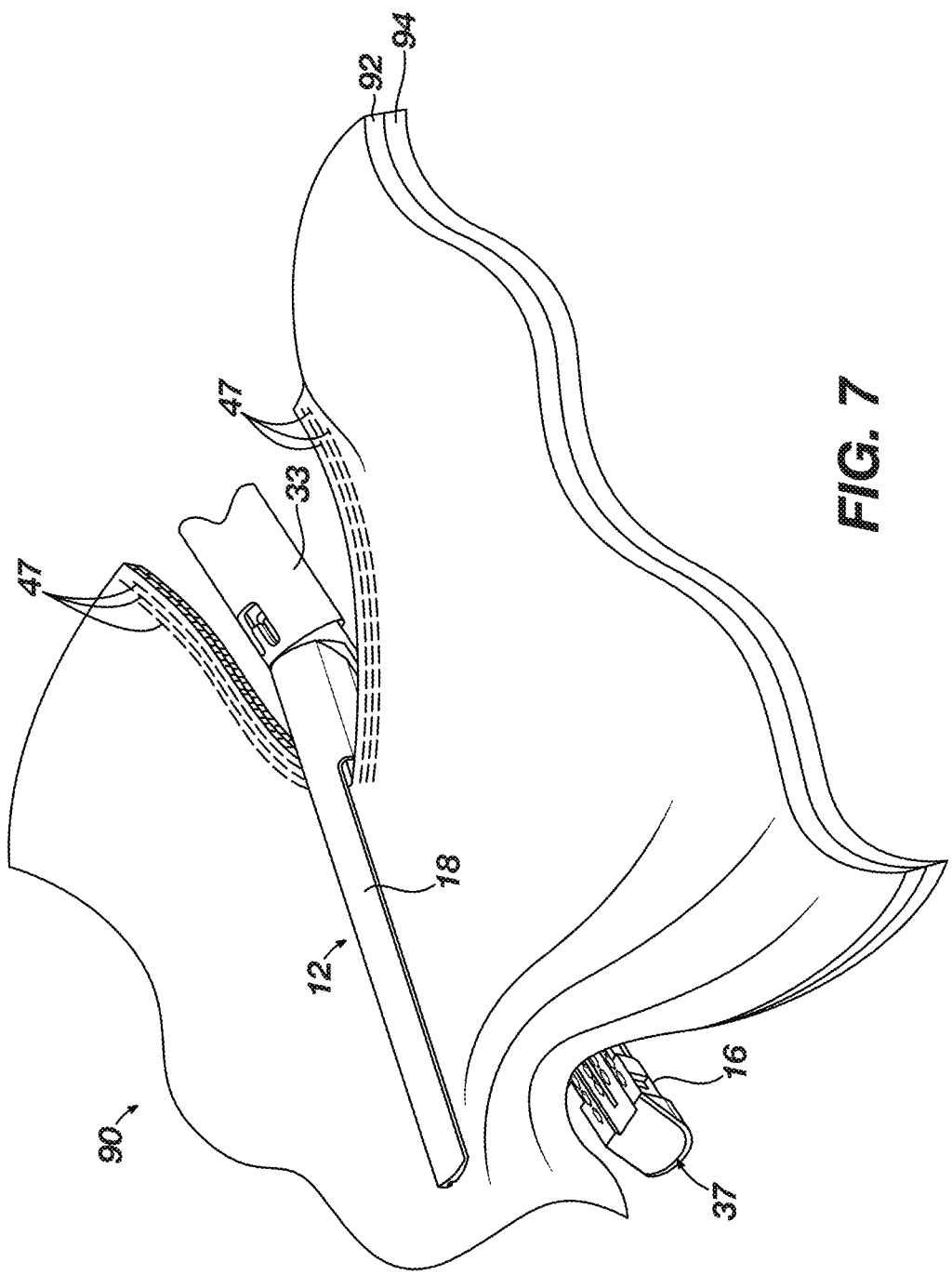
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 through tissue 90 on each side of the cut line produced by cutting edge 48. After the first firing stroke is complete, end effector 12 is withdrawn from the patient, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

Figure 8:
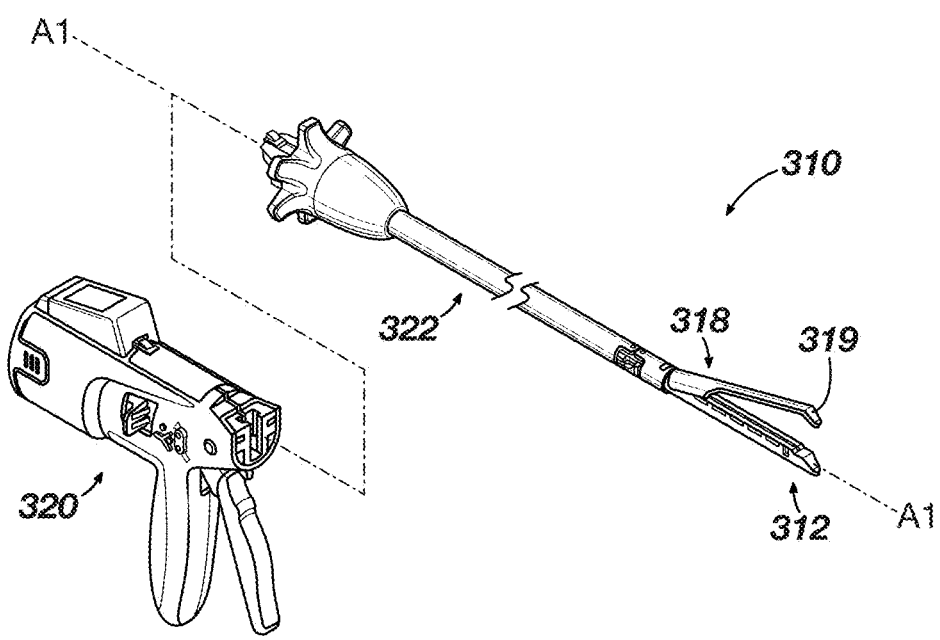
FIG. 8 depicts a perspective view of an example of a surgical stapling instrument having a modular end effector.

FIG. 8 shows another example of an instrument 310 configured as a surgical stapler. Instrument 310 includes a handle portion 320 and a shaft 322. Instrument 310 has a modular configuration such that shaft 322 is selectively removable from, and attachable to, handle portion 320. Instrument 310 is configured similarly to instrument 10 such that the operability and use of instrument 310 is the same as described above for instrument 10 with the added feature of instrument 310 being a modular configuration. With its modular configuration, instrument 310 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 310 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 310 with a modular configuration will be apparent to those of ordinary skill in the art in view of the teachings herein. Moreover, it will be understood by those of ordinary skill in the art in view of the teachings herein, that instrument 10 may be modified to incorporate a modular configuration as shown and described with respect to instrument 310 or other instruments incorporated by reference herein.

It will be appreciated that end effector 312 may be used in place of end effector 12 shown in FIG. 1. In some versions, end effector 312 may be integrally formed with shaft 22 or alternatively may be separately formed and then combined. In some versions, end effector 312 may be provided for use in robotic systems. In such robotic systems, modular shaft 322 having end effector 312 may be attachable to a portion of the robotic system for use such that handle portion 320 is replaced by components of the robotic system. Still in other examples, end effector 312 may be adapted for use with a robotic system in a manner where end effector 312 connects with the robotic system without necessarily connecting the entire modular shaft 322. In view of the teachings herein, other ways to incorporate an end effector into a user operated or robotic operated instrument will be apparent to those of ordinary skill in the art.

II. Dummy Cartridge with Load Cells for Measuring Tissue Thickness & Indicating Cartridge Selection As indicated above, staple cartridges for endoscopic surgical staplers preloaded with different size/height staples are available, and typically color coded to indicate as such, and are designed for very specific tissue thickness ranges. Choosing the correct staple height is important for making sure that grasped tissue is properly accommodated by the formed staple. If the grasped tissue is thicker than can be successfully accommodated by the staple height, the formation of the staple (referred to as the "b-form") may be too tight or small, which may cut off blood supply resulting in necrosis. If the grasped tissue is thinner than can be successfully stapled due to the staple height being too tall or wide, the formed staples may not be able to apply sufficient compression to effectively seal the tissue resulting in bleeding or oozing.

Staple cartridge selection is currently done via visual estimation by a surgeon during surgery. However, this approach to estimating tissue thickness may involve guess work by the surgeon that can lead to selecting a wrong type of staple cartridge, i.e., choosing the wrong staple size for the tissue desired to be stapled. While surgeons may employ other methods of measuring tissue thickness, those methods may take too much time, which delays the surgery, or may involve more complicated systems, such as many extra devices and/or wires needed to operate those devices.

Augmented sensing, feedback, and connectivity are desired for both robotic and handheld instruments used in both laparoscopic and open surgeries. The surgical stapling features of the present disclosure seek to enhance preoperative planning, surgical performance, therapeutic support, and training to improve patient outcomes and reduce harm. In particular, the surgical stapling features of the present disclosure augment and enhance a user's, e.g., a surgeon or a robotic system, perception of a tissue by providing contextual feedback (within or at the surgical site) to help inform intraoperative decisions based on parameters and data sensed, obtained, and displayed by a staple cartridge device.

The surgical stapling features of the present disclosure seek to enable a clinician to determine an appropriate cartridge selection quickly and precisely during or before a surgical procedure. The disclosed systems, devices, and methods involve the use of a self-contained, reusable, closed-loop tissue thickness measuring device in the form of a staple cartridge, which may be referred to herein as a "dummy cartridge" or "smart cartridge." The disclosed dummy cartridge senses mechanical load, pressure, stress, strain, or deflection via sensing implements housed within the dummy cartridge. The dummy cartridge features a visual indication of recommended cartridge size based on an internal calculation correlating measured tissue thickness to cartridge size. A user, such as a surgeon, would simply insert the dummy cartridge into a surgical stapler and clamp over the tissue they desire to staple over (in the "inverted" state, with cartridge side facing up towards an endoscope, in one example). The dummy cartridge utilizes the pressure/load/stress/strain/deflection measured to calculate the tissue thickness based on internal lookup tables on an integrated printed circuit board (PCB). The corresponding recommended tissue thickness is then indicated to the user with a simple light-emitting diode (LED) (one LED or an array of LEDs), liquid-crystal display (LCD) or LED screen, or other visualization means.

The disclosed dummy cartridge removes the guesswork of cartridge selection and allows surgeons to more accurately measure tissue rapidly during surgery. In situations where a surgeon's estimation is between two cartridge sizes, the additional data provided by the disclosed dummy cartridge allows the surgeon to select the appropriate cartridge. A more accurate and non-subjective method of evaluating tissue thickness prior to stapling may reduce bleeding/oozing (b-form of staple too large/wide) or necrosis (b-form of staple too tight/small) of the tissue. The disclosed tissue-measuring device or cartridge system may be an entirely enclosed electrical system in a cartridge body, having no wire routing or connections needed within the surgical stapler. Installation and removal of the dummy cartridge may be identical to regular staple cartridges, allowing for easy adoption and use. Since the dummy cartridge may be completely sealed, it can also be sterilized and reused.

In particular, the disclosed embodiments relate to a staple cartridge selection system, including an end effector configurable in an unclamped configuration and a clamped configuration. The end effector includes a load sensing cartridge or "dummy cartridge" insertable into a channel of a cartridge jaw of the end effector for assembly therewith. The load sensing cartridge includes a body having a proximal end portion and a distal end portion, and an elongated channel within the body between the proximal end portion and the distal end portion. A load sensor is disposed within the elongated channel of the load sensing cartridge and is configured to sense a parameter and generate data based thereon that is indicative of a tissue thickness when tissue is clamped between the anvil jaw and the cartridge jaw in the clamped configuration. In some embodiments, the load sensor includes a plurality of load cells or strain gauges or other sensors to detect pressure or other parameters indicative of tissue thickness. The load sensing cartridge also includes a visual indicator disposed at least along a portion of the load sensing cartridge, such as at the distal end portion of the load sensing cartridge. The visual indicator is configured to display visual feedback, or a visual indication, based on the parameter sensed by the load sensor. The visual feedback is indicative of a recommended staple cartridge size, thereby making cartridge selection easier and more accurate.

Figure 9:
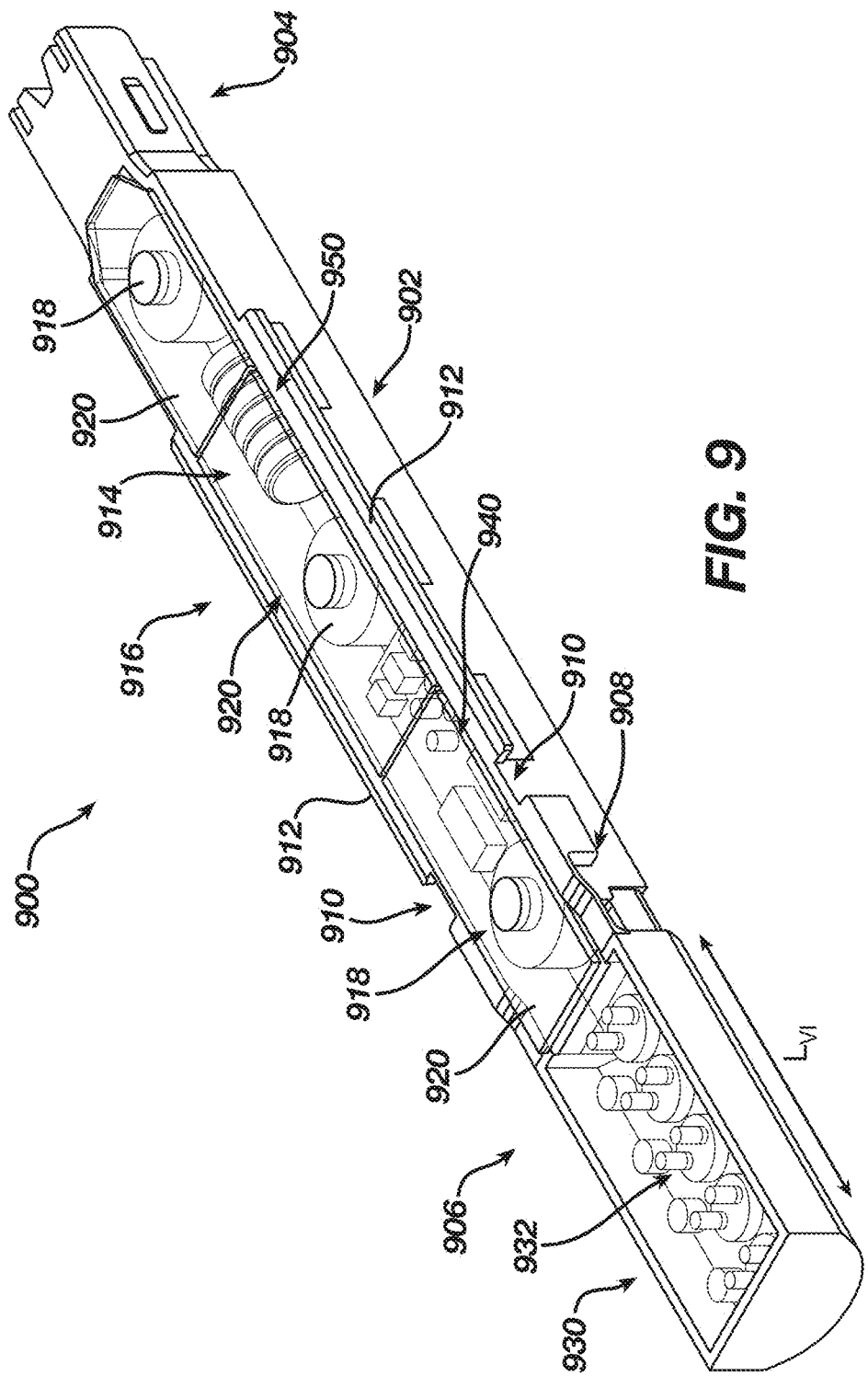
FIG. 9 depicts a perspective view of a load sensing cartridge according to one embodiment.

FIG. 9 depicts a perspective view of a load sensing cartridge, or load sensing staple cartridge, according to one embodiment. The load sensing cartridge 900 is configured to be used with an end effector, such as end effector 12 described above, having a cartridge jaw 16 and an anvil jaw 18 pivotably connected to the cartridge jaw 16 to clamp tissue, such that the end effector 12 is configurable in an unclamped configuration and a clamped configuration. The load sensing cartridge 900 (also referred to as a dummy cartridge or smart cartridge) includes a body 902 having a proximal end portion 904 and a distal end portion 906. The size and shape of the body 902 of the load sensing cartridge 900 is designed to be the same as the body 70 of a typical staple cartridge 37 described above (see FIGS. 3-6), such that the load sensing cartridge 900 is capable of being inserted into and received by a channel of a cartridge jaw 16 of an end effector 12 for assembly therewith. In this way the load sensing cartridge 900 removably fits within a jaw of a surgical stapler.

Specifically, in one example, the shape of the proximal end portion 904 is designed to be the same shape as the proximal end portion of a regular staple cartridge 37, but without having the wedge sled 41, as shown in FIGS. 4A-6. In this regard, the load sensing cartridge 900 would still trip certain lockout features, such as a "no-cartridge" or "spent-cartridge" lockout feature, which prevents operation of the end effector 12 when no cartridge is detected in the lower/cartridge jaw 16 or when a previously used (i.e., fired) cartridge is detected in the lower/cartridge jaw 16, respectively. Similarly, since the proximal end portion 904 of the load sensing cartridge 900 is designed the same, an absence of the load sensing cartridge 900 in the channel of the cartridge jaw 16 prevents the end effector 12 from being operated.

In another example, the body 902 of the load sensing cartridge 900 also includes similar, if not identical, alignment features as the body 70 of a regular staple cartridge 37, as best shown when comparing FIG. 9 with FIGS. 3 and 6 described above. For instance, the body 902 of the load sensing cartridge 900 may include alignment features such as lugs 908, notches 910, and flanges 912. Similar to the regular staple cartridge 37, the alignment features of the load sensing cartridge 900 facilitate the connection between the load sensing cartridge 900 and the channel of a cartridge jaw 16 of an end effector 12. In this way, the load sensing cartridge 900 installs and removes the same as a regular staple cartridge, such as the staple cartridge 37 described above in connection with FIGS. 3-6.

The load sensing cartridge 900 also includes an elongated channel 914 within the body 902 between the proximal end portion 904 and the distal end portion 906. The elongated channel 914 extends longitudinally through a portion of the body 902 between the proximal end portion 904 and the distal end portion 906. As shown in FIG. 9, the elongated channel 914 extends substantially the entire length of the body 902 between the proximal end portion 904 and the distal end portion 906. The load sensing cartridge 900 also includes a load sensor 916 disposed within the elongated channel 914 of the load sensing cartridge 900. The load sensor 916 is configured to sense a parameter indicative of a tissue thickness when tissue is clamped between the anvil jaw 18 and the cartridge jaw 16 in the clamped configuration, as described below with reference to FIG. 11. The parameter sensed by the load sensor 916 includes a mechanical load, pressure, stress, strain, or deflection, which is then used to calculate the tissue thickness. For example, the load sensor 916 may be a force transducer, which converts a force, such as a mechanical load, pressure, stress, strain, or deflection due to tissue being clamped, into an electrical output signal. As the force changes, the output signal changes proportionally. The load sensor 916 may include a load cell 918, such as a strain gauge load cell, hydraulic load cell, pneumatic load cell, capacitive load cell, piezoelectric load cell, or other now known or later developed load cells.

In one example, the load sensor 916 may include a plurality of load cells 918 spaced apart within the elongated channel 914 between the proximal end portion 904 and the distal end portion 906 of the load sensing cartridge 900. In the example shown in FIG. 9, three load cells 918 are used, where a first load cell 918 is disposed adjacent the distal end portion 906, a second load cell 918 is disposed adjacent the proximal end portion 904, and a third load cell 918 is disposed between the first and second load cells 918 in the middle of the elongated channel 914 of the portion of the body 902 of the load sensing cartridge 900. However, more or fewer load cells 918 may be used. Each of the plurality of load cells 918 may sense a force and output an electrical signal indicative thereof. The greater number of load cells 918 would provide more data indicative of loads applied along various portions of the load sensing cartridge 900, and thus result in a greater resolution of load data and ultimately tissue thickness. This is true whether the individual output signals are aggregated and averaged together or whether each output signal is used individually. However, space constraints in the elongated channel 914 may dictate the number of load cells 918 that may be used. In some examples, providing a load cell 918 near the proximal end portion 904 results in data indicative of tissue thickness of tissue clamped near the proximal portion of the end effector, while providing a load cell 918 near the distal end portion 906 results in data indicative of tissue thickness of tissue clamped near the distal portion of the end effector. However, the tissue targeted for thickness measurements and cartridge selection purposes may be clamped in the middle of the jaws of the end effector, thus providing a load cell 918 near the middle of the elongated channel 914 of the portion of the body 902 of the load sensing cartridge 900 may be advantageous, especially if the tissue being clamped is thick, since this could affect readings on the load cells 918 at the distal and proximate end portions 906, 908.

The load sensing cartridge 900 may also include a plurality of load plates 920 corresponding to the plurality of load cells 918. For example, each load cell 918 situated within the elongated channel 914 may have a corresponding load plate 920 disposed on top of the load cell 918 and flush with the upper portions of the sidewalls of the body 902 of the load sensing cartridge 900. The plurality of load plates 920 span across the elongated channel 914 of the load sensing cartridge 900 to form an even surface for the tissue to be clamped against. In this way, the load plates 920 act as an upper deck of the load sensing cartridge 900, similar to the upper deck 72 of the cartridge body 70 discussed above and shown in FIGS. 3, 5, and 6. The load plates 920 of FIG. 9 are shown as clear to show the components underneath the load plates 920 within the elongated channel 914.

In other embodiments, in lieu of the load cells 918 and corresponding load plates 920, other devices and methods may be used for converting tissue-loading forces into some form of electrical output signal. In one example, S-beam or cantilever beam style load cells may be used, which may be customized to fit within the elongated channel 914 of the load sensing cartridge 900. In another example, extensometers and strain gauges linked to any number of custom beams or linkages may be used. In yet another example, pressure sensing film and/or paper may be used to detect the pressure across the cartridge face (i.e., the tissue-contacting surface of the load sensing cartridge 900). The pressure sensitive film may be a pre-scale pressure film provided by Fujifilm or a thin film sensing grid provided by Tekscan.

The load sensing cartridge 900 also includes a visual indicator 930 disposed at the distal end portion 906 of the load sensing cartridge 900. The visual indicator 930 is configured to display visual feedback, or a visual indication, based on the parameter sensed by the load sensor 916, such as the load cells 918. The visual feedback indicates a recommended staple cartridge size, or range of sizes, based on the tissue thickness calculated by the internal circuitry 940, as discussed below in more detail.

In one example, the visual indicator 930 may include a light-emitting diode (LED) array of a plurality of LEDs 932 connected to a printed circuit board (PCB). In this example, each LED 932 of the LED array may correspond to a tissue thickness or range of tissue thickness. In one example, as shown in FIG. 9, the plurality of LEDs 932 include five (5) LEDs 932 arranged longitudinally in the portion of the elongated channel 914 at the distal end 906 of the body 902 of the load sensing cartridge 900 that makes up the visual indicator 930. More or less LEDs 932 may be used. In one example, a series of LEDs may be included for each load cell 918, such that each load cell 918 is associated with a particular series or arrangement of LEDs 932. For example, instead of having one series of LEDs 932 as shown in FIG. 9, the visual indicator 930 may include three series of smaller LEDs 932, such that each series corresponds to a separate load cell 918.

In one example, the visual indicator 930 may be integrally formed with (i.e., as part of) the body 902 of the load sensing cartridge 900, such that the visual indicator 930 spans most, if not all, of the distal end portion 906 of the load sensing cartridge 900. In another example, the visual indicator 930 may be a separate component from the load sensing cartridge 900 that is coupled to the distal end of the load sensing cartridge 900. In each case, either the visual indicator 930 or the portion of the body 902 of the load sensing cartridge 900 that makes up the visual indicator 930 is a certain length greater than a length of a regular cartridge, such as the staple cartridge 37 described above in connection with FIGS. 3-6. In other words, a total length of the load sensing cartridge 900 is greater than a total length of a regular cartridge by an amount equal to a length of the visual indicator 930 ($L_{VI}$ in FIG. 9). In one example, the length of the visual indicator 930 $L_{VI}$ may be 0.5 inch. In other examples, the length of the visual indicator 930 $L_{VI}$ may be longer or shorter, depending on the type of visual indicator 930 used, as described below.

The view of the visual indicator 930 in FIG. 9 shows anode and cathode elements extending upward from the bases of the LEDs 932 with the lenses/cases of the LEDs 932 facing downward. The visual indicator 930 also includes a PCB. In the example shown in FIG. 9, the PCB spans across, and connects to, the anode and cathode elements of the LEDs 932. A cover lays flat across the visual indicator 930 to protect the LEDs 932 and PCB underneath. The flat cover forms an even surface for the tissue to be clamped against. In this way, the flat cover is a part or extension of the upper deck of the load sensing cartridge 900 described above, such that the flat cover of the visual indicator 930 and the load plates 920 are flush with each other to form an even surface that makes up the upper deck of the load sensing cartridge 900.

Figure 10:
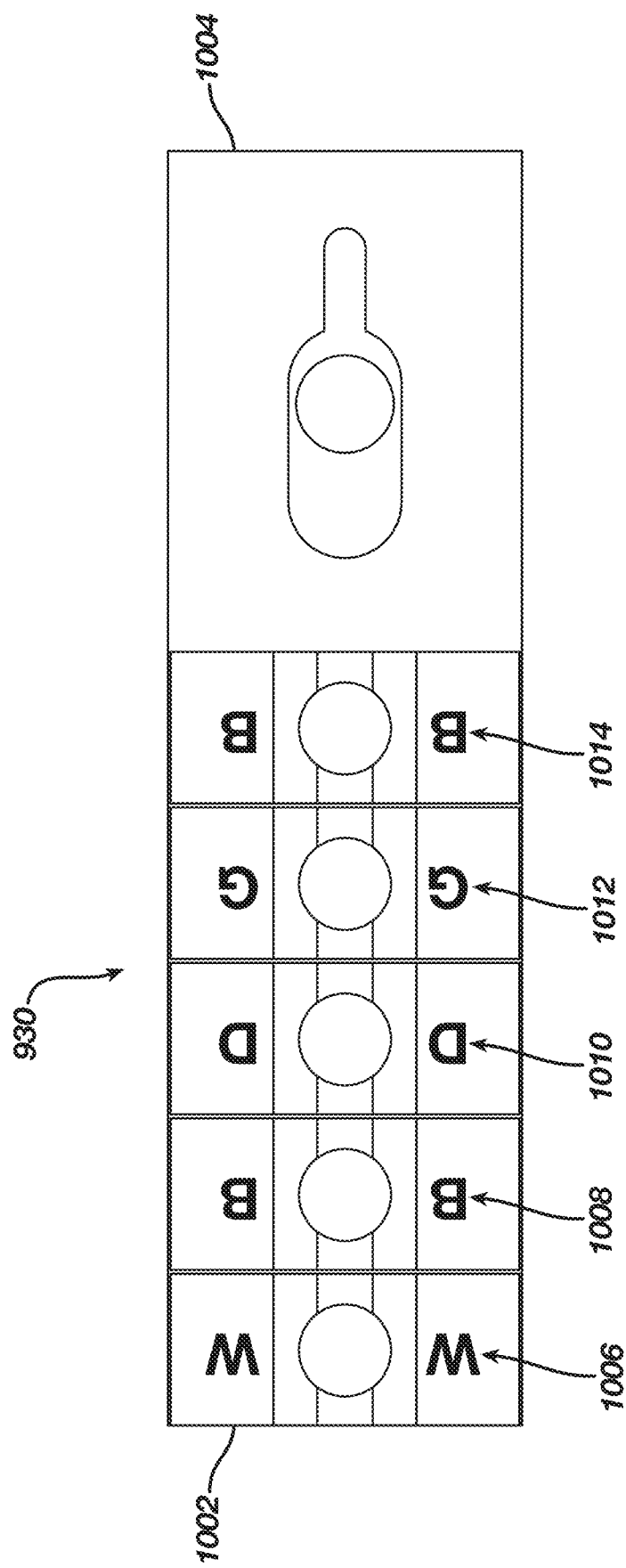
FIG. 10 depicts a plan view of a visual indicator according to one embodiment.

FIG. 10 depicts a plan view of a visual indicator 930 according to one embodiment. The view shown in FIG. 10 depicts a side of the visual indicator 930 opposite from the flat cover side shown in FIG. 9. In other words, if the view shown in FIG. 9 is a top view of the load sensing cartridge 900, and thus a top view of the visual indicator 930, the view shown in FIG. 10 is a bottom view of the visual indicator 930. As shown in FIG. 10, the lenses/cases of the LEDs 932 (the parts of the LEDs 932 that light up) are visible when viewing the visual indicator 930 from this view, as described further below with reference to FIG. 11. The visible portions of the lenses/cases of the LEDs 932 are disposed longitudinally across a portion of the length of the visual indicator 930 between a distal end 1002 and proximal end 1004 of the visual indicator 930. In another embodiment, the lenses/cases of the LEDs 932 may be arranged to face upward, such that portions of the lenses/cases of the LEDs 932 are visible through the flat cover described above. In this way, a user of the load sensing cartridge 900 would not need to invert the load sensing cartridge 900 during use (as described below with reference to FIG. 11) to see the visual feedback provided by the visual indicator 930. In yet another embodiment, LEDs 932 may be visible on both sides of the visual indicator 930 such that the visual feedback is visible from both directions.

As stated above, each LED 932 of the LED array may correspond to a tissue thickness or range of tissue thickness. In this way, each LED 932 of the LED array corresponds to a cartridge size or range of cartridge sizes. The visual indicator 930 is configured such that one LED 932 of the LED array will light up to indicate which cartridge, or cartridge range, should be selected. In order to indicate to a user of the load sensing cartridge 900 what cartridge or cartridges are within range of the tissue the load sensing cartridge 900 is clamped on, each LED 932 of the LED array is associated with a particular indicator indicative of a cartridge. In one example, the indicator may be an embossed/debossed, laser-marked, or pad-printed masking or marking that is disposed on the visual indicator 930 adjacent (i.e., next to) each respective LED 932. For example, if staple cartridges are color-coded, where certain colors of staple cartridges indicate the size of staples held therein to properly seal corresponding tissue thicknesses, the embossed/debossed, laser-marked, or pad-printed masking or marking next to each LED 932 may be a single letter corresponding to a staple cartridge color. This example is shown in FIG. 10, where a letter is disposed on both sides of each LED 932.

FIG. 10 shows an embodiment of an LED array having five LEDs 932, where each LED 932 has a letter disposed on both sides of the LED 932. A first LED 932 at the distal end 1002 of the visual indicator 932 includes a white letter "W" 1006. The white letter "W" 1006 may correspond to the color white, which may be a color of a staple cartridge having a certain size of staples corresponding to a certain tissue thickness. Thus, if the first LED 932 next to the letter "W" 1006 lights up, this indicates to the user of the load sensing cartridge 900 that they should select a white staple cartridge for the tissue clamped within the load sensing cartridge 900. A second LED 932 (in the distal direction from the first LED 932) includes a blue letter "B" 1008. The blue letter "B" 1008 may correspond to the color blue, which may be a color of a staple cartridge having a certain size of staples corresponding to a certain tissue thickness different than that of the white staple cartridge. Thus, if the second LED 932 next to the blue letter "B" 1008 lights up, this indicates to the user of the load sensing cartridge 900 that they should select a blue staple cartridge for the tissue clamped within the load sensing cartridge 900. A third LED 932 (in the distal direction from the second LED 932) includes a gold letter "D" 1010. The gold letter "D" 1010 may correspond to the color gold, which may be a color of a staple cartridge having a certain size of staples corresponding to a certain tissue thickness different than that of the white and blue staple cartridges. Thus, if the third LED 932 next to the letter "D" 1010 lights up, this indicates to the user of the load sensing cartridge 900 that they should select a gold staple cartridge for the tissue clamped within the load sensing cartridge 900. A fourth LED 932 (in the distal direction from the third LED 932) includes a green letter "G" 1012. The green letter "G" 1012 may correspond to the color green, which may be a color of a staple cartridge having a certain size of staples corresponding to a certain tissue thickness different than that of the white, blue, and gold staple cartridges. Thus, if the fourth LED 932 next to the letter "G" 1012 lights up, this indicates to the user of the load sensing cartridge 900 that they should select a green staple cartridge for the tissue clamped within the load sensing cartridge 900. A fifth LED 932 (in the distal direction from the fourth LED 932) includes a black letter "B" 1014. The black letter "B" 1014 may correspond to the color black, which may be a color of a staple cartridge having a certain size of staples corresponding to a certain tissue thickness different than that of the white, blue, gold and green staple cartridges. Thus, if the fifth LED 932 next to the black letter "B" 1014 lights up, this indicates to the user of the load sensing cartridge 900 that they should select a black staple cartridge for the tissue clamped within the load sensing cartridge 900. In another example, the black letter "B" may be replaced with a different letter, such as "K," so as to not be confused with the blue letter "B" discussed above (i.e., similar to using "D" for gold rather than "G," which is used for green).

In the example shown in FIG. 10, each respective letter 1006-1014 has a unique color. In other examples, the colors of all the letters may be the same. In this case, each letter may be unique, and the letter alone may indicate a certain color of staple cartridge to select.

In another example, rather than (or in addition to) having letters next to the LEDs 932, the LEDs 932 themselves may be specific colors, where each color of the LEDs 932 corresponds to certain staple cartridges. For instance, using the same LED array in FIG. 10 and the same staple cartridge color examples, the first LED 932 may be a white LED 932, such that the first/white LED 932 lighting up indicates to the user to select a white staple cartridge. Similarly, the second LED 932 may be a blue LED 932, such that the second/blue LED 932 lighting up indicates to the user to select a blue staple cartridge. The third LED 932 may be a gold LED 932, such that the third/gold LED 932 lighting up indicates to the user to select a gold staple cartridge. The fourth LED 932 may be a green LED 932, such that the fourth/green LED 932 lighting up indicates to the user to select a green staple cartridge. The fifth LED 932 may be a purple LED 932, such that the fifth/purple LED 932 lighting up indicates to the user to select a black staple cartridge.

The indications described above would be the same in the example mentioned above of having a series of LEDs included for each load cell 918. In this case, each load cell 918 is associated with a particular series or arrangement of LEDs 932, and the visual indicator 930 may include three series of smaller LEDs 932, such that each series corresponds to a separate load cell 918. In this case, each series of LEDs 932 may have the same functionality and structure as described above, albeit smaller in terms of size so that all three series of LEDs 932 may fit on the visual indicator 930.

In another embodiment, the visual indicator 930 may include a liquid-crystal display (LCD) or light-emitting diode (LED) screen, as opposed to individual LEDs. In this example, the LCD or LED screen is also configured to provide the visual feedback based on the parameter sensed by the load sensor 916, such as the load cells 918. Referring back to FIG. 10, the LCD or LED screen would take the place of the five LEDs and corresponding letters 1006-1014, such that the screen would face outward from the underside of the load sensing cartridge 900, similar to the direction the light from the LEDs 932 shine in FIG. 10 (i.e., out of the page). The electronic circuitry and components of the LCD or LED screen would be housed inside the visual indicator 930, similar to where the LEDs 932 and PCB of FIG. 9 are located. In the example of using an LCD or LED screen, the size of the visual indicator 930 may be reduced, depending on the type of output on the LCD or LED screen. For instance, if the indication or visual feedback provided by the LCD or LED screen is a single letter, such as the letters discussed above with reference to FIG. 10, the LCD or LED screen may be sized smaller since the screen would only need to be large enough to display a single letter. In another example, the LCD or LED screen may be configured to simply illuminate the entire screen the color of the recommended cartridge selection, such as white, blue, gold, green, and the like. In this case, the screen size may be reduced as well, such as the size of a single LED 932. In yet another example, the LCD or LED screen may be configured to display a simplified word, such as "BLU" or "GRN" to indicate the color blue or green, respectively. In yet still another example, the LCD or LED screen may be configured to display an entire word, such as "WHITE", or an entire product code for a particular staple cartridge, such as the product code for a gold staple cartridge. In this way, the LCD or LED screen provides the visual feedback indicating the recommended staple cartridge size by displaying a product code, simplified word, or color corresponding to a particular cartridge size to the user of the load sensing cartridge 900.

In yet another embodiment of indicating tissue thickness via the visual indicator 930, rather than the LED array or LDC/LED screen discussed above, a single multi-color LED may be used. In this example, the single multi-color LED would change to a particular color to indicate cartridge selection, such as blue for selecting a blue staple cartridge, white for selecting a white staple cartridge, purple for selecting a black staple cartridge, and the like. For the example of indicating cartridge size for each load cell 918, three multi-color LEDs may be used, where each multi-color LED is associated with a separate load cell 918.

Referring back to FIG. 9, the load sensing cartridge 900 also includes internal circuitry 940 disposed within the elongated channel 914. In one example, the internal circuitry 940 may be a load sensing PCB. The internal circuitry 940 is electrically connected to the load sensor 916, such as the load cells 918, so that the output signals generated by the load cells 918 in response to pressure (e.g., tissue clamping force) are sent to the internal circuitry 940 via the electrical connection. In one example, as shown in FIG. 9, the internal circuitry 940 is disposed between the first load cell 918 adjacent the distal end portion 906 and the third load cell 918 in the middle of the elongated channel 914 of the body 902 of the load sensing cartridge 900. However, in other examples the internal circuitry 940 may be disposed in other portions of the elongated channel 914, such as between the third/middle load cell 918 and the second load cell 918 adjacent the proximal end portion 904 or anywhere space in the elongated channel 914 allows. The internal circuitry 940 is also electrically connected to the PCB of the visual indicator 930, such that the internal circuitry 940 can send electrical signals to the PCB of the visual indicator 930, as described below.

The internal circuitry 940, which may be entirely analog or a combination of analog and digital components, is configured to calculate the tissue thickness based on the mechanical load, pressure, stress, strain, or deflection sensed by the load sensor 916. The internal circuitry 940 calculates the tissue thickness by correlating the sensed mechanical load, pressure, stress, strain, or deflection to a corresponding tissue thickness. For example, preprogrammed internal lookup tables may be stored in a memory of the internal circuitry 940 and used to calculate tissue thickness. An internal lookup table may map input values (e.g., sensed mechanical load, pressure, stress, strain, or deflection) to output values (e.g., tissue thickness). Another internal lookup table may map other input values (e.g., tissue thickness) to other output values (e.g., suggested cartridge).

For example, given one set of input values, such as the output signals from the load cells 918 containing sensed force or pressure, a lookup operation using the internal lookup tables retrieves the corresponding output values from the table, such as tissue thickness. Another lookup operation may be performed using another lookup table, where the input value is the tissue thickness output from the first lookup operation and the output value is a corresponding cartridge selection (e.g., type, size, color, name, product code, and the like). In this way, the internal circuitry 940 is configured to determine the recommended staple cartridge size by correlating the calculated tissue thickness to a corresponding staple cartridge size.

In particular, the load cells 918 may be electrically connected (e.g., wired) to a controller on the load sensing PCB (i.e., internal circuitry) 940. The controller may be configured to receive the output signals, e.g., analog signals, from the load cells 918 and process the signals using the internal lookup tables to calculate the tissue thickness of the clamped tissue. In one example, the controller may aggregate and average the output signals (i.e., force readings) from all of the load cells 918 and use the average value as the input for the lookup tables. In this case, the internal circuitry 940 may calculate a single tissue thickness based on an average of all data from all of the load cells 918. In another example, the controller may receive individual output signals from each load cell 918 and use each of those values as the input for the lookup tables. In this case, the internal circuitry 940 may calculate tissue thickness for each load cell 918.

In certain instances, the controller may include a microprocessor ("processor") and one or more computer readable mediums or memory units ("memory") coupled therewith. In certain instances, the memory may store various program instructions, which when executed, may cause the processor to perform a plurality of functions and/or calculations described herein.

In certain instances, the controller may be at least partially digital. In some examples, the controller may be implemented utilizing dedicated hardware, such as one or more of discrete components, an integrated circuit, an application-specific integrated circuit (ASIC), a programmable logic device (PLD), a processor executing firmware instructions, a processor executing software instructions, or any combination thereof. When implemented utilizing a processor executing software or firmware instructions, the software or firmware instructions may be stored in any suitable computer readable memory such as on a magnetic disk, an optical disk, or other storage medium, etc. The software or firmware instructions may include machine readable instructions that, when executed by one or more processors, cause the one or more processors to perform various acts related to detecting sensed mechanical load, pressure, stress, strain, or deflection based on the signals from the load cells 918, including data indicative of measurements obtained using the plurality of load cells 918, to provide instructions to the PCB of the visual indicator 930 in order to provide visual feedback to a user of load sensing cartridge 900, such as to illuminate an LED 932 of the LED array based on the calculated tissue thickness, etc. In some implementations, the controller may include one or more digital to analog converters (DACs) and one or more analog to digital converters (ADCs) configured to convert signals between analog signals suitable for use with the load cells 918 and digital signals used with digital circuitry of the controller and other components of the internal circuitry 940, as well as the digital circuitry of the PCB of the visual indicator 930.

As mentioned above, the internal circuitry 940 is also configured to send electrical signals to the PCB of the visual indicator 930. Thus, the internal circuitry 940 and PCB of the visual indicator 930 communicate with one another via electronic signals in order to illuminate an LED 932 of the LED array based on the calculated tissue thickness (or thicknesses). In particular, once the internal circuitry 940 calculates the tissue thickness and corresponding cartridge selection as described above, the controller generates and sends a signal indicative of the cartridge selection to the PCB of the visual indicator 930. A controller on the PCB of the visual indicator 930 receives this signal indicative of the cartridge selection and then, in response to receiving this signal, illuminates one of the LEDs 932 corresponding to the cartridge selection. In this way, the illuminated LED 932 provides the visual feedback to the user indicating the recommended staple cartridge size. In the example of having a series of LEDs 932 for each load cell 918, the same process disclosed above is repeated for each load cell 918. In other words, the internal circuitry 940 calculates the tissue thickness and corresponding cartridge selection as described above for each individual load cell 918, and then the controller generates and sends a signal indicative of the cartridge selection to the PCB of the visual indicator 930 for each load cell 918. A controller on the PCB of the visual indicator 930 receives these signals indicative of the cartridge selection for each load cell 918 and then, in response to receiving these signals, illuminates one of the LEDs 932 corresponding to the cartridge selection on each series of LEDs.

The internal circuitry 940 of the load sensing cartridge 900 may also be programmed such that multiple types of logic can be applied as to what is indicated or otherwise displayed to the user. For instance, in addition to or in lieu of indicating a cartridge selection based on tissue thickness, the load sensing cartridge 900 may also display or indicate other types of information.

In one example, logic may be programmed on the internal circuitry 940 to display a warning message or provide a warning indicator. For example, when battery levels of batteries powering the load sensing cartridge 900, discussed below, are below recommended levels, an automatic warning message (or indication) may be provided to the user. In one example, the warning message may be a message displayed on the LDC/LED screen, such as "LOW BATTERY," "LOW BATT," "BATT," an icon of a battery, or any other message or display that indicates a low battery level. In another example, the LED array may be used to indicate a low battery level. For example, a specific arrangement/number of LEDs may light up or blink to indicate a low battery. In one example, all LEDs of the LED array may light up or blink (simultaneously, alternatingly, or in some other prearranged order). For instance, immediately upon being inserted into the cartridge jaw and powering on, a certain number of LEDs may illuminate for a short period to indicate battery life. In this example, if all five LEDs of the LED array lit up, that could indicate full battery level. If, on the other hand, only one LED of the LED array lit up, that could indicate low battery level. In other words, the number of LEDs that light up correspond to the battery level, where more illuminated LEDs is indicative of more battery life and less illuminated LEDs is indicative of lower battery life. In another example, a single LED, such as the cartridge selection LED, may blink to indicate a low battery. In this example, the blink rate may be indicative of the battery level, where a fast blink rate indicates full power and a slow blink rate indicates low power, or vice versa. In yet another example, the visual indicator 930 may have a separate LED specifically for indicating a low battery. These types of warning messages or indications may, for example, prevent a brownout from affecting reading accuracy. In another example, the load sensing cartridge 900 may shut down when battery levels are below a certain level.

Another circumstance where a warning message or indication may be appropriate is when uneven tissue loading beyond a recommended threshold is present. For example, if the user clamps the jaws on tissue and there is more tissue (i.e., thicker tissue) in one particular end of the jaws, such as in the back, or proximal end, of the jaws or, in the alternative, in the distal end of the jaws, this would be a situation of uneven tissue loading. Having too much of uneven tissue loading is not desired, since staples in a given staple cartridge are uniform for that cartridge, meaning that if a staple cartridge is selected for the thick tissue present at one end of the jaws, the staple size will not be appropriate for the thinner tissue present elsewhere in the jaws. As stated above, if a staple height is too tall or wide, the formed staples may not be able to apply sufficient compression to effectively seal the tissue resulting in bleeding or oozing. Likewise, if a staple cartridge is selected for the thinner tissue, the staple size will not be appropriate for the thicker tissue present at elsewhere in the jaws. In this case, the selected staple may be too tight or small for the thicker tissue, which may cut off blood supply resulting in necrosis. Thus, having a warning message or indication of uneven tissue loading may help inform the user that they should reposition the stapler and re-clamp with the load sensing cartridge 900.

The warning message for uneven tissue loading may be a message displayed on the LDC/LED screen, such as "UNEVEN TISSUE," "UNEVEN," "ERROR-REPOSITION," "REPOSITION," or any other message or display that indicates uneven tissue between the jaws. The message may even indicate where along the jaws the thicker/thinner tissue is located (i.e., proximal, middle, or distal). In another example, the LED array may be used to indicate uneven tissue within the jaws. For example, a specific arrangement/number of LEDs may light up or blink to indicate uneven tissue, similar to those described above for low batter level. In one example, the LEDs corresponding to the location of the thicker tissue may illuminate. For example, if the tissue between the jaws is thicker at the distal end of the jaws, one or more LEDs at the distal end of the visual indicator 930 may light up and/or blink to indicate a warning that tissue is thicker in that area (i.e., the distal end). Similarly, if the tissue between the jaws is thicker at the proximal end of the jaws, one or more LEDs at the proximal end of the visual indicator 930 may light up and/or blink to indicate a warning that tissue is thicker in that area (i.e., the proximal end). If the tissue between the jaws is thicker in the middle of the jaws, one or more LEDs in the middle of the visual indicator 930 may light up and/or blink to indicate a warning that tissue is thicker in that area (i.e., the middle).

Another type of logic that may be programmed on the internal circuitry 940 relates to when the sensed tissue loading (i.e., the sensed mechanical load, pressure, stress, strain, or deflection) corresponds to tissue thickness associated with more than one cartridge size range. For instance, when there is tissue loading at the boundary of two cartridge size ranges, the preprogrammed logic may cause the internal circuitry 940 to indicate both cartridge sizes to the user. This may be done by illuminating two LEDs 932 of the LED array on the visual indicator 930 or by displaying two cartridge size indicators (e.g., "WHITE" and "BLUE") on the LCD/LED screen on the visual indicator 930. This allows the user (i.e., surgeon) to use their medical judgement to "round up" or "round down" on cartridge sizes. For example, if the visual indicator 930 indicates two cartridge sizes, one surgeon may decide to choose the cartridge having bigger staples, which allows for the thicker tissue to not be stapled too tight, even if this may sacrifice tightness in the areas of thinner tissue. On the other hand, under the same scenario, another surgeon may choose the opposite and select a cartridge having smaller staples in order to ensure tight staples throughout the entire tissue, even if it means the thicker tissue may be stapled tighter than desired.

Another type of logic that may be programmed on the internal circuitry 940 involves when, and for how long, the LEDs 932 or LCD/LED screen or screens illuminate. For example, one type of logic, or instructions programmed and stored on the internal circuitry 940, instructs the visual indicator 930 (whether it be the LED array or LCD/LED screen) to not light up until after a certain time period from when pressure/force (i.e., tissue loading) is first detected. For instance, once the jaws of the end effector having the load sensing cartridge 900 is clamped onto tissue, no lights will turn on until after that certain time frame has elapsed. This delay after tissue clamping ensures that the "stabilized" tissue thickness is measured (i.e., that the load is detected, resulting in the calculated tissue thickness from the internal lookup tables corresponding force detected to tissue thickness) after a majority of fluid has evacuated the clamped tissue. In one example, this predetermined time period for waiting for fluid to evacuate may be 15 seconds. A shorter or longer time period may be used. During this predetermined wait time, one or more LEDs 932 of the LED array or the LCD/LED screen may blink to indicate the load sensing cartridge 900 is waiting. The LCD/LED screen may also display a message, such as "WAIT," during this time period. Once the time period ends, the load cells 918 detect the force, send an output signal that is received by one or more PCBs (e.g., load sensing PCB and/or PCB of the visual indicator 930), which then results in the indicator being displayed to the user, either in the form of one or more illuminated LEDs 932 of the LED array or a message on the LCD/LED screen.

In another example, logic may be programmed on the internal circuitry 940 that keeps the visual indicator 930 (e.g., LED(s) 932 or LCD/LED screen) illuminated for a certain time period or until the load sensing cartridge 900 is removed from the channel of the lower jaw. This allows enough time for the surgeon to remove the end effector from the surgical site and see the indicator displayed on the visual indicator 930. Having the load sensing cartridge 900 automatically turn off after a certain time period or when the load sensing cartridge 900 is removed also saves battery life.

Referring back to FIG. 9, the load sensing cartridge 900 also includes a power source 950 for powering the components of the load sensing cartridge 900, such as the load sensor 916 or load cells 918, the visual indicator 930, and the internal circuitry 940. In one example, as shown in FIG. 9, the power source 950 may be an array of batteries, such as six (6) 1.5 volt button cell batteries. In another example, other numbers and types of batteries may be used. The power source 950, such as the batteries, may be replaceable and/or rechargeable.

Powering on the load sensing cartridge 900 may happen in a number of ways. In one example, a physical or mechanical switch may be included on the load sensing cartridge 900 to turn the load sensing cartridge 900 on. Any type of physical or mechanical switch may be used, such as a SPST (Single Pole Single Throw) switch, SPDT (Single Pole Double Throw) switch, toggle switch, slide switch, pushbutton switch, dome switch, limit switch, and the like. For example, a dome switch may be disposed somewhere on the body 902 of the load sensing cartridge 900 such that the pressure of inserting the load sensing cartridge 900 into the channel of the lower jaw activates the dome switch and turns the load sensing cartridge 900 on. In another example, a user may activate the physical or mechanical switch prior to or after inserting the load sensing cartridge 900 into the channel of the lower jaw, depending on the location of the switch (i.e., if the switch is accessible after the load sensing cartridge 900 is inserted into the channel of the lower jaw, the user may activate it after the load sensing cartridge 900 is installed, otherwise the switch may need to be activated before installing the load sensing cartridge 900).

In another example, rather than a physical or mechanical switch, an electrical, magnetic, or electromagnetic switch may be used. In this case, as soon as the load sensing cartridge 900 is inserted into the channel of the lower jaw, electrical or magnetic connections are made, which results in the load sensing cartridge 900 turning on. For example, a Hall effect sensor may be disposed within the load sensing cartridge 900 and a magnet may be disposed in the end effector, such that when the load sensing cartridge 900 is inserted into the channel of the lower jaw, the magnet trips the Hall effect sensor (i.e., the Hall effect sensor senses the magnetic field of the magnet), thus causing the load sensing cartridge 900 to turn on. In another example, a sensor may be disposed in the load sensing cartridge 900 that is configured to send a signal to turn the load sensing cartridge 900 on when metal is sensed or detected. In this way, as soon as the load sensing cartridge 900 comes in close proximity to metal, such as the jaws of the end effector, the load sensing cartridge 900 would turn on.

Figure 11:
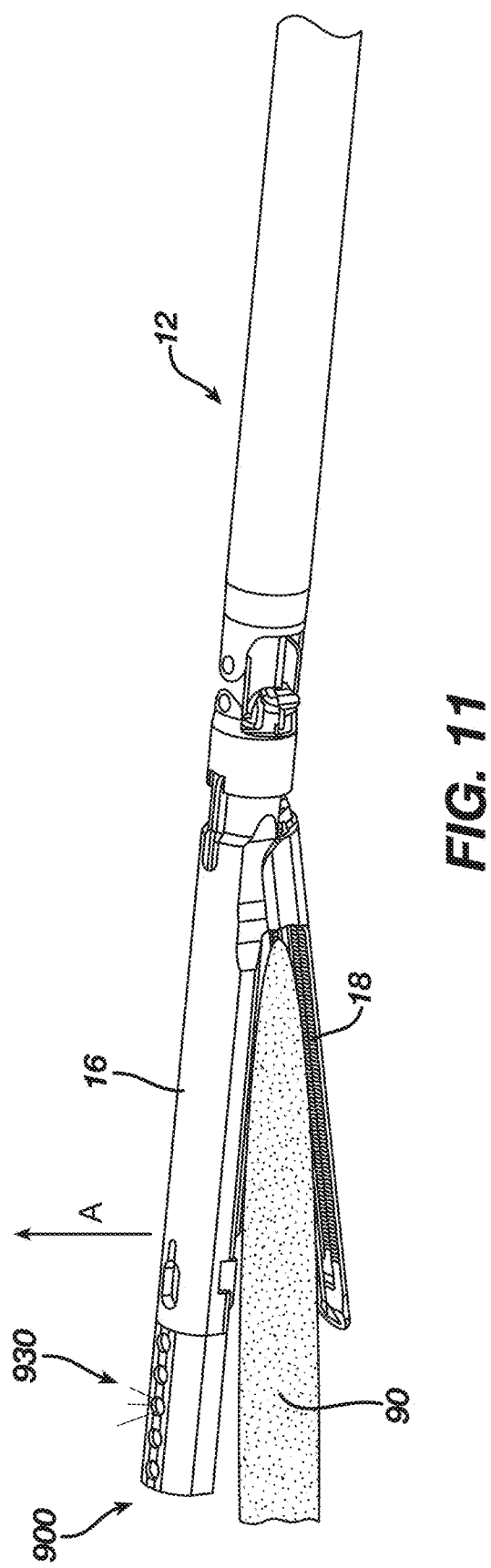
FIG. 11 depicts a perspective view of a load sensing cartridge installed in an end effector, positioned at tissue, according to one embodiment.

FIG. 11 depicts a perspective view of a load sensing staple cartridge installed in an end effector, positioned at tissue. As shown in FIG. 11, after the load sensing staple cartridge 900 is removably attached to (i.e., fit within) the lower jaw 16 of the end effector 12, a user (e.g., surgeon or robotic system) directs the end effector 12 to the desired target tissue 90. The user then clamps the tissue 90 with the end effector 12 in an inverted state (i.e., the cartridge jaw 16 facing "up" towards the endoscope, as shown by arrow A in FIG. 11) with the tissue 90 between the cartridge jaw 16 and the anvil or upper jaw 18 (which in this case is facing "down"), as shown in FIG. 11. One or more load sensors 916 of the load sensing staple cartridge 900 is configured to sense a parameter and generate data based thereon indicative of a tissue thickness when the tissue 90 is clamped between the upper jaw 18 and lower jaw 16 of the end effector 12 assembled with the load sensing staple cartridge 900. A visual indicator 930 at the distal end 906 of the load sensing staple cartridge 900 is configured to selectively illuminate based on the parameter sensed by the one or more load sensors 916, such that the visual indicator 930 indicates to a user of the load sensing staple cartridge 900 a recommended staple cartridge type for the clamped tissue 90. The end effector 12 is used in this inverted state so that the visual indicator 930 also faces "up" toward the user and/or endoscope, such that the user can see and read the visual indicator 930. This method is described in more detail below with regard to FIG. 12. However, as mentioned above, if the visual indicator 930 is configured such that the LED(s) or LCD/LED screen are disposed on a surface of the visual indicator 930 flush with the load plates 920, the end effector 12 would not need to be used in this inverted state. Rather, the user may clamp the tissue with the end effector 12 in a normal state (i.e., the cartridge jaw 16 facing "down") with the tissue 90 between the cartridge jaw 16 and the anvil or upper jaw 18 (which in this case would face "up" towards the endoscope). In one embodiment, the LED(s) or LCD/LED screen may be disposed and visible on both sides of the visual indicator 930 such that the visual feedback is visible from both directions.

Figure 12:
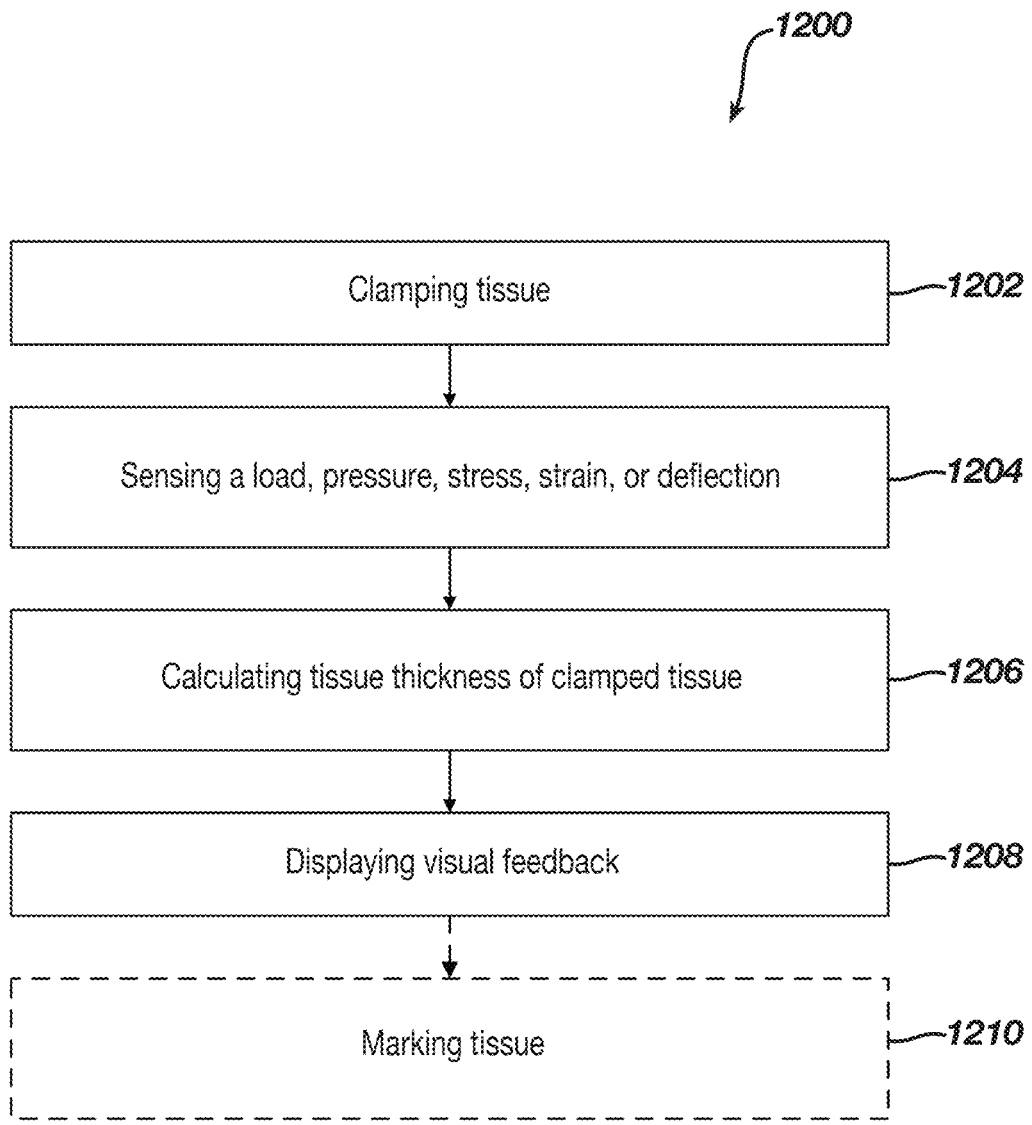
FIG. 12 is a flowchart of a method of determining staple cartridge selection according to one embodiment.

FIG. 12 is a flowchart of a method 1200 of determining staple cartridge selection according to one embodiment. In one embodiment, the method 1200 is implemented by the controller of the load sensing PCB (i.e., internal circuitry) 940 to determine tissue thickness and corresponding cartridge size for the tissue grasped between the lower jaw 16 and the anvil jaw 18 of the end effector 12 of FIGS. 9 and 11 used with the surgical instrument 10 of FIG. 1. It is noted, however, that the method 1200 may be implemented by a controller different from the controller of the load sensing PCB (i.e., internal circuitry) 940 and/or with an end effector different from the end effector 12 and/or with a surgical instrument different from the surgical instrument 10, in other embodiments. For example, the method 1200 may be implemented using the controller of the PCB of the visual indicator 930.

The method 1200 may include clamping tissue 90 with an end effector 12 including a cartridge jaw 16 and an anvil jaw 18 pivotably connected to the cartridge jaw 16, where the cartridge jaw 16 includes a load sensing cartridge 900 inserted therein (Block 1202). As described above with respect to FIG. 11, the tissue 90 is clamped with the end effector 12 in an inverted state (i.e., the cartridge jaw 16 facing "up") with the tissue 90 between the cartridge jaw 16 and the anvil or upper jaw 18 (the latter of which would be facing "down"), as shown in FIG. 11. Clamping in this inverted state with the visual indicator 930 facing "up" toward the user and/or endoscope allows the user to see and read the visual indicator 930.

The method 1200 may further include sensing, by one or more load sensors 916 of the load sensing cartridge 900, a mechanical load, pressure, stress, strain, or deflection (Block 1204). Once the tissue 90 is clamped and pressure of the tissue 90 (i.e., tissue loading) is detected, the load cells 918 sense or detect the mechanical load, pressure, stress, strain, or deflection after a predetermined wait time, such as 15 seconds, to allow fluid to evacuate from the clamped tissue 90. As described above, the load cells 918, upon sensing a load, converts the load into an electrical output signal, which is sent to the internal circuitry 940 (i.e., load sensing PCB).

The method 1200 may further include calculating, by a processor of the load sensing cartridge 900, a tissue thickness of the clamped tissue 90 based on the sensed mechanical load, pressure, stress, strain, or deflection (Block 1206). The processor or controller of the internal circuitry 940 of the load sensing cartridge 900 uses internally stored lookup tables to calculate the tissue thickness and corresponding recommended staple cartridge. In this way, calculating the tissue thickness includes correlating the sensed mechanical load, pressure, stress, strain, or deflection to a corresponding tissue thickness. Specifically, the sensed load value in the output signal is used as the input to a first table, where the output is a tissue thickness. The method 1200 further includes determining the recommended staple cartridge by correlating the calculated tissue thickness to a corresponding staple cartridge. Similar to calculating the tissue thickness, determining the recommended staple cartridge includes inputting, by processor or controller of the internal circuitry 940 of the load sensing cartridge 900, the calculated tissue thickness into another internally stored lookup table, where the output is the recommended staple cartridge.

The method 1200 may further include displaying, by a visual indicator 930 of the load sensing cartridge 900, visual feedback, or a visual indication, based on the parameter sensed by the one or more load sensors 916, wherein the visual feedback is indicative of a recommended staple cartridge (Block 1208). The processor or controller of the internal circuitry 940 calculates the tissue thickness based on the parameter sensed by the one or more load sensors 916 using the first lookup table and then uses the output from the second lookup table discussed above to instruct the visual indicator 930 to display the recommended staple cartridge as the visual feedback. In one embodiment, displaying the visual feedback may include illuminating one or more light-emitting diodes (LEDs) 932 disposed in or on the load sensing cartridge 900. The illuminated LED 932 may indicate a staple cartridge size in a number of ways, as discussed above. In another embodiment, displaying the visual feedback may include displaying a message on an LCD/LED screen. Various types of messages may be displayed, as discussed above.

The visual indicator 930 may display the visual feedback for a predetermined time to allow the user enough time to read the visual feedback. This amount of time may vary but should be long enough to allow the user to remove the endocutter with the end effector 12 having the load sensing cartridge 900 from the body of the patient to ensure proper reading of the visual feedback. The visual indicator 930 may turn off after this predetermined amount of time to conserve battery life. Removing the load sensing cartridge 900 from the end effector 12 may also power down all components of the load sensing cartridge 900. The load sensing cartridge 900 may be sterilized and re-used for subsequent measurements.

While the embodiments discussed above relate to a self-contained, closed-loop tissue thickness measuring device that senses parameters and generates and sends signals to other components contained in the device in order to display an indication on the device itself, it is contemplated that the signals generated based on the sensed parameters may be sent to a computer and/or display elsewhere, such as in the operating room. For example, the disclosed load sensing cartridge 900 may also include a transmitter operable to wirelessly send the electrical output signals generated based on the parameters sensed by the one or more load sensors 916 to a processor in a computer station in the operating room. In this case, the visual indication or feedback may also be displayed on a display connected to the computer station. This type of display may be larger than any visual indicator 930 on the load sensing cartridge 900, which allows additional data to be displayed, such as charts, graphs, and/or entire words, sentences, or paragraphs.

Further, while the embodiments discussed above describe LED(s) or an LCD/LED screen disposed on one of two surfaces of the visual indicator 930 (i.e., a surface along the same plane as the cartridge deck or a surface along the same plane as the underside surface of the cartridge deck 16), LEDs may be provided along a length of the load sensing cartridge 900, such as at or near the top of the sidewalls that define the elongated channel 914. In this case, the light from the LEDs may illuminate or reflect off the clamped tissue. In another example, flanges, such as flanges 912 discussed above, may be configured to extend outward a certain distance from the load sensing cartridge 900, such that LEDs may be disposed along the length of the flanges on the underside thereof so as to be visible when the end effector 12 is used in the inverted state.

III. Wired Reusable Smart Cartridge to Access Tissue Thickness

In certain types of surgical procedures, such as open surgeries, it may be advantageous to digitally enable an open mechanical or surgical device, such as an open surgical stapler, as increased data collection may be highly valuable. However, wirelessly sending data, such as via Bluetooth, from a smart or "dummy" cartridge from inside a human body may have limitations. For instance, when the dummy cartridge is behind organs or between tissue, the wireless signal may become attenuated with the tissue and fluid and becomes difficult to send and receive. To overcome these limitations, the signal may be sent to the handle of the surgical device, which is located outside of the body, (ideally by wire) and then may be transmitted (wirelessly or via a wire) elsewhere, such as to a computer station in the operating room.

The proposed dummy cartridge features a wired cartridge having the same dimensions of existing stapler cartridges. The features of the proposed dummy cartridge are similar to the dummy or smart cartridge described in the section above, except that the proposed dummy cartridge described below involves a dummy cartridge for an open surgical stapler and has a wired connection to a piece of equipment in the operating room, such a generator tower, to provide power and data communication to the dummy cartridge and to link the dummy cartridge to a display or user interface to allow a user of the dummy cartridge to see the data collected by the dummy cartridge. As described below, the wired connection allows for continuous power and improved and constant data collection/communication.

The proposed dummy cartridge is easy to use since users of surgical stapling devices are accustomed to replacing cartridges. The proposed standalone device may also reduce the cost of goods required for adding sensors to existing devices, such as staplers or staple cartridges, as well as wires requiring continuous impact to normal ergonomics of the device.

The dummy cartridge described herein may be used for training feedback, clamp load detection, to assess the viability of targeted tissue, and to increase confidence before firing an actual staple cartridge. For example, feedback from the dummy cartridge may be displayed on a screen for a user to view, which may help inform the user on what type of staple cartridge should be used for the targeted tissue. After using the dummy cartridge and reading/evaluating the feedback provided by it, the dummy cartridge is easily removed and replaced with an actual staple cartridge with staples inserted and used with increased confidence.

The proposed dummy cartridge may be re-sterilized depending on the sensitivity and robustness of the compression sensor circuitry, such as the internal circuitry 940 discussed above. In one example, a re-sterilization process similar to harmonic transducer handpiece sterilization may be used. The packaging of the dummy cartridge may also mirror the packaging of handpieces (sold non-sterile). In this case, a counter may be provided that limits the number of uses to the designed lifetime of the device.

Figure 13:
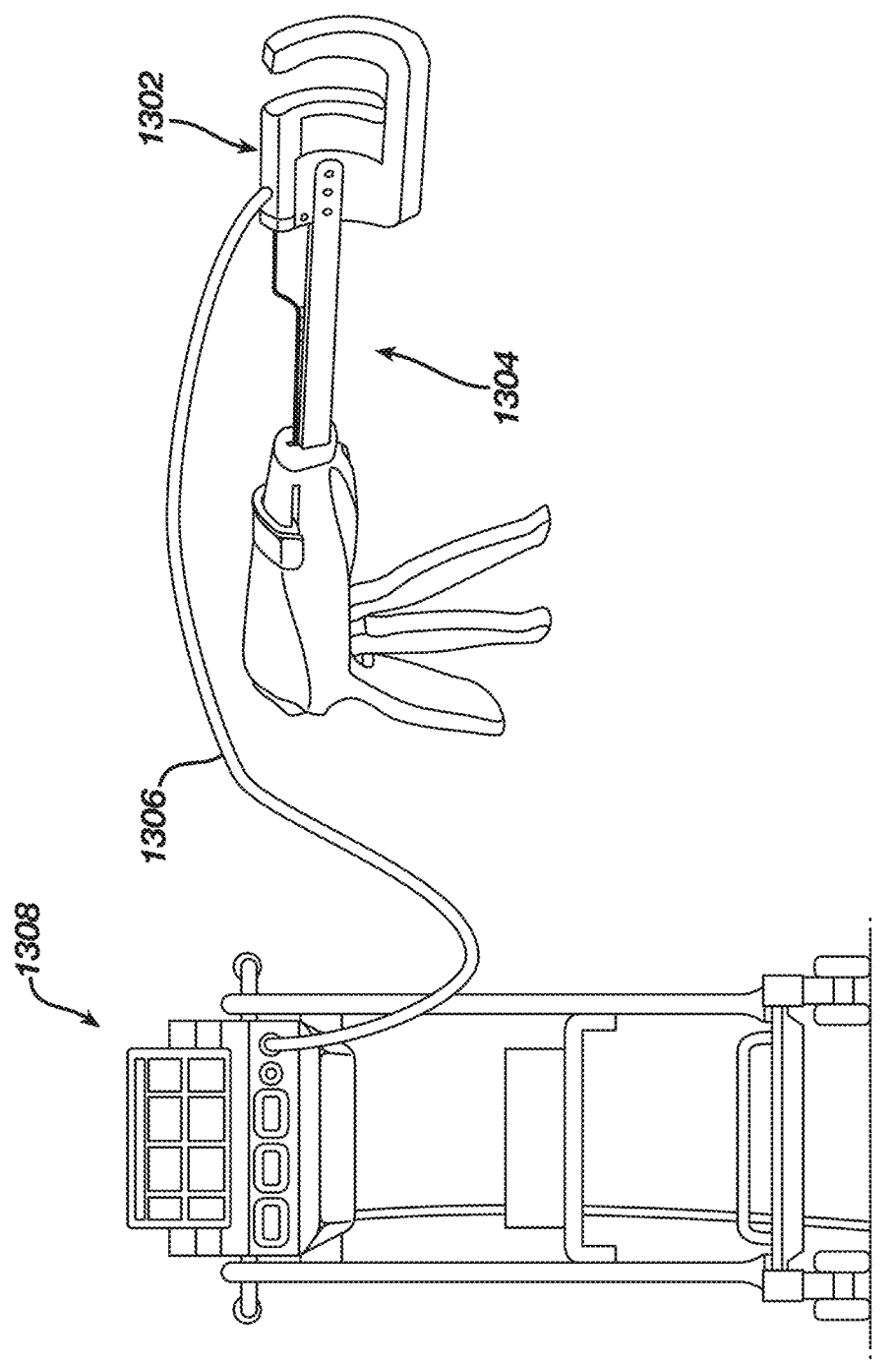
FIG. 13 depicts a perspective view of a wired dummy cartridge for use in an open surgical stapler according to one embodiment.

FIG. 13 depicts a perspective view of a wired dummy cartridge for use in an open surgical stapler according to one embodiment. As shown in FIG. 13, a load sensing staple cartridge 1302 is removably fit within a jaw of a surgical stapler 1304 for assembly therewith. The load sensing staple cartridge 1302 may be similar to the load sensing cartridge 900 described in the section above. For example, the load sensing staple cartridge of FIG. 13 may include one or more load sensors configured to sense a parameter and generate data based thereon indicative of a tissue thickness when tissue is clamped between jaws of the surgical stapler 1304 assembled with the load sensing staple cartridge 1302. The parameter sensed by the one or more load sensors may include a mechanical load, pressure, stress, strain, or deflection caused by the jaws of the surgical stapler 1304 clamping on tissue. The sensed parameter may then be used to calculate the tissue thickness. Similar to above, the one or more load sensors may be one or more force transducers, which convert a force, such as a mechanical load, pressure, stress, strain, or deflection due to tissue being clamped, into an electrical output signal.

As shown in FIG. 13, the load sensing staple cartridge 1302 is connected, by wire 1306, to a device 1308 nearby. In one example, the device 1308 may be a power station, such as a generator tower. In this regard, the device 1308 is operable to supply power to the load sensing staple cartridge 1302 as soon as, and for as long as, the load sensing staple cartridge 1302 is plugged into the device 1308 via the wire 1306. The device 1308 is also operable to communicate data to and from the load sensing staple cartridge 1302 via the wire 1306. For example, the load sensing staple cartridge 1302 may send data through the wire 1306 to the device 1308. Thus, the one or more load sensors are configured to sense a parameter, generate a signal based thereon (analog or digital), and send the signal to a processor configured to calculate the tissue thickness based on the sensed parameter and to calculate a recommended staple cartridge type for the clamped tissue based on the calculated tissue thickness.

In one example, the device 1308 may include a processor configured to receive and process data sent by the load sensing staple cartridge 1302. For example, the processor of the device 1308 may be configured to calculate tissue thickness in the same manner as described in the section above. For instance, the processor may be configured to calculate the tissue thickness based on a mechanical load, pressure, stress, strain, or deflection sensed by the one or more load sensors. The processor of the device 1308 may also be configured to calculate a recommended staple cartridge type in a similar fashion as described above as well.

In another example, the load sensing staple cartridge 1302 may include internal circuitry similar to the internal circuitry 940 discussed above. In this case, the internal circuitry of the load sensing staple cartridge 1302 may include a processor configured to calculate the tissue thickness and calculate a recommended staple cartridge.

In one embodiment, the device 1308 may include, or be connected to, a display or user interface. The recommended staple cartridge type for the clamped tissue, calculated by the processor, may be displayed to a user of the load sensing staple cartridge 1302 on the display or user interface. In this way, the load sensing staple cartridge 1302 is connected to the display and a power source via a wired connection, such as the wire 1306.

Having a display or user interface as opposed to the LED array or LCD/LED screen discussed above provides additional benefits. For example, more options and different types of data may be displayed on the display or user interface, which is much larger than the LCD/LED screen discussed above. For instance, rather than a short word, entire phrases or sentences pertaining to a recommended staple cartridge may be shown on the display. Further, graphs and charts may be displayed on the display as well. For instance, the entire lookup tables for tissue thickness and staple cartridge selection calculations may be shown on the display. In this case, the calculated tissue thickness and recommended staple cartridge may be highlighted, which allows the user (e.g., surgeon) to see how the cartridge selection was made and to be able to make informed decisions, such as rounding up or down, accordingly. This allows surgeons to make decisions based on information and data being visually displayed in a more pleasing manner. Additionally, data logging infrastructure may be utilized to track tissue thickness data over the course of many procedures to gain clinical insights.

Since the load sensing staple cartridge 1302 is connected to power via a wire 1306, not only does the load sensing staple cartridge 1302 have instantaneous and continuous power from being plugged in to unplugged, but the wire also 1306 reduces the need for batteries and on/off switches, as described above. This allows more room on the load sensing staple cartridge 1302 for additional load sensors. As described above, more load sensors result in more sensed parameters and generated data based thereon, which results in improved and higher resolution data. The increased, and continually read, data is easily handled by the wire 1306, which is another advantage of the wired connection. The disclosed dummy cartridge may also include multiplexors to handle the additional data.

As mentioned above, the proposed dummy cartridge 1302 may be re-sterilized and re-used. The wire 1306 and connection components may also be re-sterilized and re-used. In this case, the wire 1306 may be removable from the load sensing staple cartridge 1302 and the device 1308.

IV. Smart Cartridge for Tissue Sensing and Marking

As was noted above, once the thickness is determined, the instrument is unclamped and removed from the body so that the appropriate staple cartridge may be inserted. The instrument is then placed back in the body and repositioned around the same tissue which was just measured so as to complete the procedure. In some instances, once the tissue thickness is calculated and a staple cartridge selection is recommended, it may be difficult to know the exact location where the tissue reading was performed due to the characteristics of the tissue, e.g., the tissue may have different variability (ability to stretch and shape), biphasic characteristics (both liquid and solid characteristics), or varying thickness. Thus, another problem exists the ability to locate the tissue that was just measured in order to complete the surgical procedure. It may be advantageous to be able to mark tissue after calculating tissue thickness and confirming an area to be fired on with an actual reload (i.e., actual staple cartridge containing staples). Therefore, there is a need for a dedicated, diagnostic device that assesses tissue thickness, improves staple load selection, and has the ability to mark tissue to transect.

The proposed smart cartridge involves a reusable tissue measuring and marking linear cutter/stapler cartridge. This smart cartridge has pressure sensing ability with either embedded micro load cells, pressure pads, or the like, as discussed in the sections above, and measures the pressure when clamped on desired tissue. The proposed smart cartridge also includes tissue marking pens or other devices embedded in the cartridge that can be actuated once the surgeon confirms the tissue is within the desired thickness and uniformity that they want to fire on. The proposed smart cartridge may then be removed from the device and a normal staple reload loaded, placed on the marked tissue and fired.

Figure 14:
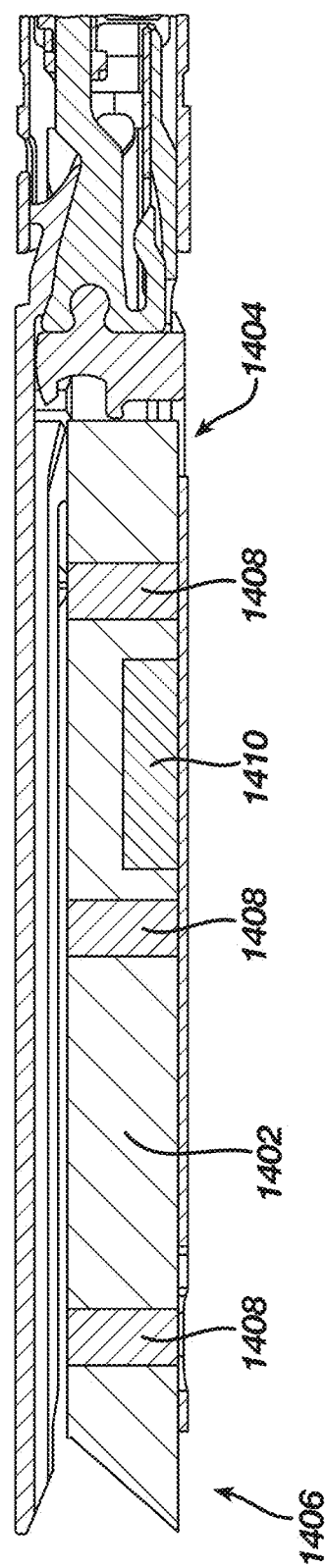
FIG. 14 depicts a side cross-sectional view of another load sensing cartridge according to one embodiment.

FIG. 14 depicts a side cross-sectional view of another load sensing cartridge according to one embodiment. In the embodiment shown in FIG. 14, the smart cartridge 1402 includes pressure sensors 1408, such as load cells for sensing tissue compression, at a number of locations between the proximal end 1404 and distal end 1406 of the smart cartridge 1402 to show tissue thickness uniformity and overall tissue thickness. Three pressure sensors 1408 are shown in FIG. 14, but more or fewer sensors may be used. The pressure sensors 1408 may be the same as the load sensors 916 discussed above and include load cells such as the load cells 918 discussed above. The smart cartridge 1402 may also include a microprocessor 1410 embedded into the smart cartridge 1402 body. The microprocessor 1410 may be the same as the load sensing PCB/internal circuitry 940 discussed above. The microprocessor 1410 may include a wireless communication system, such as Bluetooth or similar near field communication (NFC) capabilities. In one example, if the surgical stapling device that the smart cartridge 1402 is removably assembled with includes an electrical connection, such as at the proximal end of the staple cartridge channel, the smart cartridge 1402 may also include an electrical connection point at the proximal end 1404 thereof and communicate with the surgical stapling device via the electrical connection point.

Figure 15:
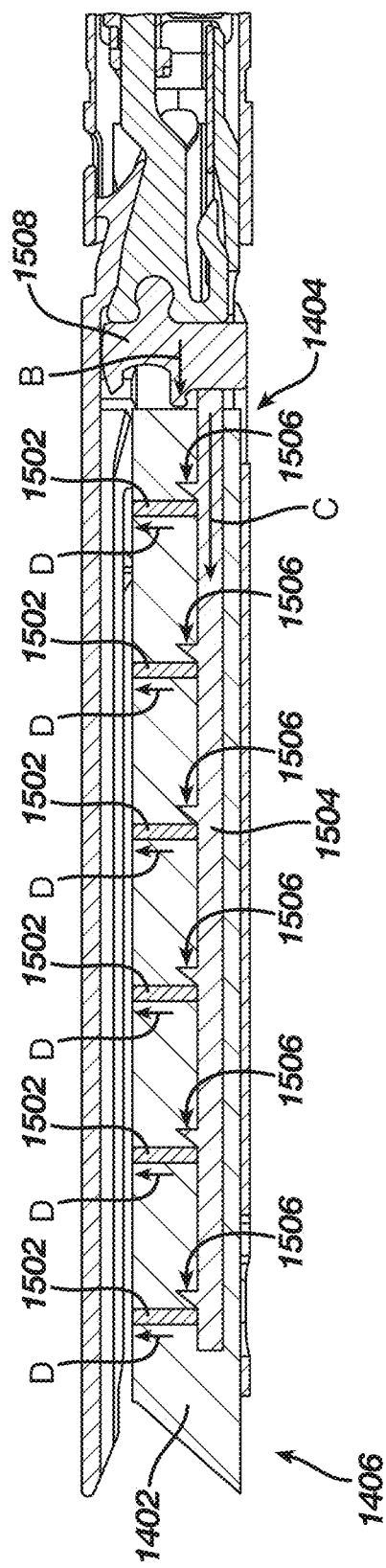
FIG. 15 depicts a side cross-sectional view of the load sensing cartridge of FIG. 14 having tissue marking tips that are deployed mechanically.

FIG. 15 depicts a side cross-sectional view of the load sensing cartridge of FIG. 14 having tissue marking tips. As shown in FIG. 15, the smart cartridge 1402 also includes a plurality of deployable tissue marking tips 1502 at a number of locations between the proximal end 1404 and distal end 1406 of the smart cartridge 1402. The deployable tissue marking tips 1502 are configured to mark an area that a user (i.e., surgeon or robotic system) selects to fire across once tissue thickness readings are acquired (as described above) and an actual staple cartridge is loaded into the surgical stapling device. This allows the user to know the exact location of where the tissue reading was performed so that once the surgical stapling device is removed from the targeted tissue and the smart cartridge 1402 is removed and replaced with an actual staple cartridge, the user can navigate the surgical stapling device back to where the readings were performed and fire on the tissue that is marked by the deployable tissue marking tips 1502.

The tissue marking tips 1502 may be deployed by either mechanical or electromechanical means. In a mechanical example, as shown in FIG. 15, the smart cartridge 1402 may include a wedge driver 1504 disposed near the base of the smart cartridge 1402 and include a number of raised protrusions 1506 having an inclined, angled, or cambered surface disposed adjacent, on the proximal side, the tissue marking tips 1502. A portion of the wedge driver 1504 may extend from the proximal end 1404 of the smart cartridge 1402 in line with the knife 1508 of the surgical stapling device. In this way, a small amount of movement by the knife 1508 in the distal direction (as shown by the arrow B in FIG. 15), prior to engaging a lockout feature, contacts the portion of the wedge driver 1504 extending in the proximal direction and advances the wedge driver 1504 in the distal direction (as shown by the arrow C in FIG. 15), which causes the inclined, angled, or cambered surfaces of the raised protrusions 1506 to contact the tissue marking tips 1502. As the inclined, angled, or cambered surfaces of the raised protrusions 1506 contact the tissue marking tips 1502, the tissue marking tips 1502 are moved upwards (as shown by the arrows D in FIG. 15) such that the tissue marking tips 1502 contact and mark the tissue. These movements of the knife 1508, wedge driver 1504 and tissue marking tips 1502 are shown by the arrows B, C, and D, respectively, in FIG. 15.

Figure 16:
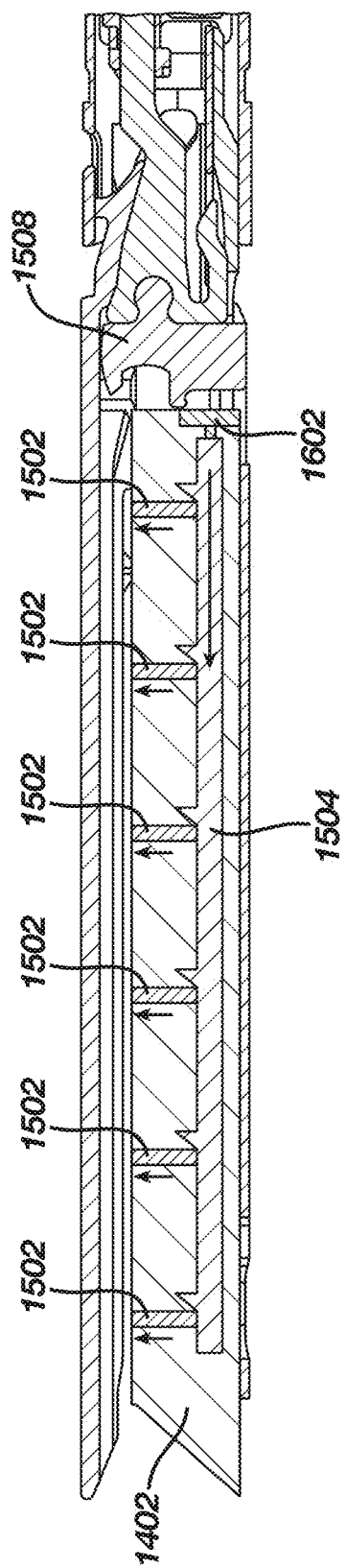
FIG. 16 depicts a side cross-sectional view of the load sensing cartridge of FIG. 14 having tissue marking tips that are deployed electromechanically.

In another example, as shown in FIG. 16, the tissue marking tips 1502 are deployed electromechanically. As shown in FIG. 16, the smart cartridge 1402 includes a powered actuator 1602. The powered actuator 1602 includes an electrical connection to either a power source located in the smart cartridge 1402, such as the power source 950 described above with regard to FIG. 9, or an external power source electrically connected to the smart cartridge 1402 via the electrical connection point described above. The powered actuator 1602 causes the same movement of the wedge driver 1504 and tissue marking tips 1502 described above, causing the tissue marking tips 1502 to be moved upwards such that the tissue marking tips 1502 contact and mark the tissue, as shown by the arrows in FIG. 16. In this way, the powered actuator 1602 replaces the need for the knife 1508 to move and contact a portion of the wedge driver 1402 extending outside the smart cartridge 1402 in the proximal direction.

In yet another embodiment, each tissue marking tip 1502 may be deployed (i.e., driven) by an electromagnet. In one example, a magnet may be located at the base of each tissue marking tip 1502 and electromagnets having the same pole as the magnets in the base of the tissue marking tip 1502 may be located in the smart cartridge 1402 under the bases of the tissue marking tips 1502 (or alternatively in the wedge driver 1504 at locations corresponding to the bases of the tissue marking tips 1502). An electrical signal may be applied to the electromagnets, which would cause the electromagnets and the magnets in the bases of the tissue marking tips 1502 to repel one another, thus causing the tissue marking tips 1502 to be moved upwards such that the tissue marking tips 1502 contact and mark the tissue, as shown by the arrows in FIG. 16.

In the examples described above, the smart cartridge 1402 containing the deployable tissue marking tips 1502 may be reusable, such that the smart cartridge 1402 can be used multiple times in the same procedure, or sterilized and used in a different procedure, before being discarded.

The tissue marking tips 1502 described above may be used with the staple cartridge selection system described above. For example, the load sensing cartridge 900 may further include a plurality of deployable tissue markers disposed within the elongated channel 914. The plurality of deployable tissue markers may be configured to be actuated to mark the tissue 90 to indicate where the tissue thickness was calculated. In other words, the load sensing staple cartridge 900 may further include a plurality of tissue markers configured to mark the tissue 90 to indicate where the tissue thickness was calculated.

Similarly, the method 1200 of determining staple cartridge selection described above with respect to FIG. 12 may optionally include marking, by tissue markers of the load sensing cartridge 900, the clamped tissue 90 (Block 1210). Marking the clamped tissue 90 may be done mechanically or electromechanically, as described above with reference to FIGS. 15 and 16. For example, marking the clamped tissue may include advancing a wedge driver of the load sensing cartridge 900 distally to actuate the tissue markers toward the clamped tissue 90, such that the tissue markers contact and mark the tissue 90.

VI. Examples of Combinations

The following examples/clauses relate to various non-exhaustive ways in which the teachings herein may be combined or applied. It should be understood that the following examples/clauses are not intended to restrict the coverage of any claims that may be presented at any time in this application or in subsequent filings of this application. No disclaimer is intended. The following examples/clauses are being provided for nothing more than merely illustrative purposes. It is contemplated that the various teachings herein may be arranged and applied in numerous other ways. It is also contemplated that some variations may omit certain features referred to in the examples/clauses below. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

1. A staple cartridge selection system, comprising:
   an end effector configurable in an unclamped configuration and a clamped configuration, the end effector comprising:
      a cartridge jaw; and
      an anvil jaw pivotably connected to the cartridge jaw to clamp tissue; and
   a load sensing cartridge insertable into a channel of the cartridge jaw of the end effector for assembly therewith, the load sensing cartridge comprising:
      a body having a proximal end portion and a distal end portion;
      an elongated channel within the body between the proximal end portion and the distal end portion;
      a load sensor disposed within the elongated channel of the load sensing cartridge, the load sensor configured to sense a parameter indicative of a tissue thickness when tissue is clamped between the anvil jaw and the cartridge jaw in the clamped configuration; and
      a visual indicator configured to display a visual indication based on the parameter sensed by the load sensor.

2. The staple cartridge selection system of claim 1, wherein the parameter sensed by the load sensor includes a mechanical load, pressure, stress, strain, or deflection to calculate the tissue thickness.

3. The staple cartridge selection system of claim 2, further comprising internal circuitry disposed within the elongated channel, the internal circuitry being configured to calculate the tissue thickness based on the mechanical load, pressure, stress, strain, or deflection sensed by the load sensor.

4. The staple cartridge selection system of claim 3, wherein the internal circuitry is configured to:
   calculate the tissue thickness by correlating the sensed mechanical load, pressure, stress, strain, or deflection to a corresponding tissue thickness; and
   determine the recommended staple cartridge size by correlating the calculated tissue thickness to a corresponding staple cartridge size.

5. The staple cartridge selection system of claim 1, wherein the load sensor comprises a plurality of load cells spaced apart within the elongated channel between the proximal end portion and the distal end portion of the load sensing cartridge.

6. The staple cartridge selection system of claim 5, further comprising a plurality of load plates corresponding to the plurality of load cells, wherein the plurality of load plates spans across the elongated channel of the load sensing cartridge to form an even surface for the tissue to be clamped against.

7. The staple cartridge selection system of claim 5, wherein the load sensing cartridge further comprises a plurality of deployable tissue markers disposed within the elongated channel, wherein the plurality of deployable tissue markers is configured to be actuated to mark the tissue to indicate where the tissue thickness was calculated.

8. The staple cartridge selection system of claim 1, wherein the visual indicator is disposed at the distal end portion of the load sensing cartridge, and wherein the visual indication indicates a recommended staple cartridge size based on the parameter sensed by the load sensor.

9. The staple cartridge selection system of claim 8, wherein the visual indicator comprises a light-emitting diode (LED) array of a plurality of LEDs, and wherein each LED of the LED array corresponds to a range of tissue thickness.

10. The staple cartridge selection system of claim 9, further comprising internal circuitry disposed within the elongated channel, the internal circuitry being configured to calculate the tissue thickness based on the parameter sensed by the load sensor and to illuminate an LED of the LED array based on the calculated tissue thickness, such that the illuminated LED provides the visual indication indicating the recommended staple cartridge size.

11. The staple cartridge selection system of claim 1, wherein the visual indicator comprises a liquid-crystal display (LCD) or light-emitting diode (LED) screen, wherein the LCD or LED screen is configured to provide the visual indication based on the parameter sensed by the load sensor.

12. The staple cartridge selection system of claim 11, wherein the visual indication indicates a recommended staple cartridge size based on the parameter sensed by the load sensor, and wherein the LCD or LED screen provides the visual indication indicating the recommended staple cartridge size by displaying a product code, simplified word, or color corresponding to a particular cartridge size.

13. A load sensing staple cartridge configured to removably fit within a jaw of a surgical stapler for assembly therewith, the load sensing staple cartridge comprising:
   one or more load sensors configured to sense a parameter indicative of a tissue thickness when tissue is clamped between jaws of the surgical stapler assembled with the load sensing staple cartridge,
   wherein the one or more load sensors are configured to send the sensed parameter to a processor configured to calculate the tissue thickness based on the sensed parameter and to calculate a recommended staple cartridge type for the clamped tissue based on the calculated tissue thickness.

14. The load sensing staple cartridge of claim 13, wherein the processor is configured to calculate the tissue thickness based on a mechanical load, pressure, stress, strain, or deflection sensed by the one or more load sensors.

15. The load sensing staple cartridge of claim 13, wherein the recommended staple cartridge type for the clamped tissue is displayed to a user of the load sensing staple cartridge on a display.

16. The load sensing staple cartridge of claim 15, wherein the load sensing staple cartridge is connected to the display and a power source via a wired connection.

17. A method of determining staple cartridge selection, the method comprising:
   clamping tissue with an end effector comprising a cartridge jaw and an anvil jaw pivotably connected to the cartridge jaw, wherein the cartridge jaw comprises a load sensing cartridge inserted therein;
   sensing, by one or more load sensors of the load sensing cartridge, a mechanical load, pressure, stress, strain, or deflection;
   calculating, by a processor of the load sensing cartridge, a tissue thickness of the clamped tissue based on the sensed mechanical load, pressure, stress, strain, or deflection; and displaying, by a visual indicator of the load sensing cartridge, visual feedback based on the tissue thickness calculated by the processor, wherein the visual feedback is indicative of a recommended staple cartridge.

18. The method of claim 17, wherein calculating the tissue thickness comprises correlating the sensed mechanical load, pressure, stress, strain, or deflection to a corresponding tissue thickness, the method further comprising:

determining the recommended staple cartridge by correlating the calculated tissue thickness to a corresponding staple cartridge.

19. The method of claim 17, wherein displaying the visual feedback comprises illuminating one or more light-emitting diodes (LEDs) disposed in or on the load sensing cartridge.

20. The method of claim 17, further comprising marking, by tissue markers of the load sensing cartridge, the clamped tissue.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467,648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A staple cartridge selection system, comprising:
an end effector configurable in an unclamped configuration and a clamped configuration, the end effector comprising:
a cartridge jaw; and
an anvil jaw pivotably connected to the cartridge jaw to clamp tissue; and
a load sensing cartridge insertable into a channel of the cartridge jaw of the end effector for assembly therewith, the load sensing cartridge comprising:
a body having a proximal end portion and a distal end portion;
an elongated channel within the body between the proximal end portion and the distal end portion;
a load sensor disposed within the elongated channel of the load sensing cartridge, the load sensor configured to sense a parameter indicative of a tissue thickness when tissue is clamped between the anvil jaw and the cartridge jaw in the clamped configuration; and
a visual indicator configured to display a visual indication based on the parameter sensed by the load sensor.

2. The staple cartridge selection system of claim 1, wherein the parameter sensed by the load sensor includes a mechanical load, pressure, stress, strain, or deflection to calculate the tissue thickness.

3. The staple cartridge selection system of claim 2, further comprising internal circuitry disposed within the elongated channel, the internal circuitry being configured to calculate the tissue thickness based on the mechanical load, pressure, stress, strain, or deflection sensed by the load sensor.

4. The staple cartridge selection system of claim 3, wherein the internal circuitry is configured to:
calculate the tissue thickness by correlating the sensed mechanical load, pressure, stress, strain, or deflection to a corresponding tissue thickness; and
determine the recommended staple cartridge size by correlating the calculated tissue thickness to a corresponding staple cartridge size.

5. The staple cartridge selection system of claim 1, wherein the load sensor comprises a plurality of load cells spaced apart within the elongated channel between the proximal end portion and the distal end portion of the load sensing cartridge.

6. The staple cartridge selection system of claim 5, further comprising a plurality of load plates corresponding to the plurality of load cells, wherein the plurality of load plates spans across the elongated channel of the load sensing cartridge to form an even surface for the tissue to be clamped against.

7. The staple cartridge selection system of claim 5, wherein the load sensing cartridge further comprises a plurality of deployable tissue markers disposed within the elongated channel, wherein the plurality of deployable tissue markers is configured to be actuated to mark the tissue to indicate where the tissue thickness was calculated.

8. The staple cartridge selection system of claim 1, wherein the visual indicator is disposed at the distal end portion of the load sensing cartridge, and wherein the visual indication indicates a recommended staple cartridge size based on the parameter sensed by the load sensor.

9. The staple cartridge selection system of claim 8, wherein the visual indicator comprises a light-emitting diode (LED) array of a plurality of LEDs, and wherein each LED of the LED array corresponds to a range of tissue thickness.

10. The staple cartridge selection system of claim 9, further comprising internal circuitry disposed within the elongated channel, the internal circuitry being configured to calculate the tissue thickness based on the parameter sensed by the load sensor and to illuminate an LED of the LED array based on the calculated tissue thickness, such that the illuminated LED provides the visual indication indicating the recommended staple cartridge size.

11. The staple cartridge selection system of claim 1, wherein the visual indicator comprises a liquid-crystal display (LCD) or light-emitting diode (LED) screen, wherein the LCD or LED screen is configured to provide the visual indication based on the parameter sensed by the load sensor.

12. The staple cartridge selection system of claim 11, wherein the visual indication indicates a recommended staple cartridge size based on the parameter sensed by the load sensor, and wherein the LCD or LED screen provides the visual indication indicating the recommended staple cartridge size by displaying a product code, simplified word, or color corresponding to a particular cartridge size.

13. A load sensing staple cartridge configured to removably fit within a jaw of a surgical stapler for assembly therewith, the load sensing staple cartridge comprising:
one or more load sensors configured to sense a parameter indicative of a tissue thickness when tissue is clamped between jaws of the surgical stapler assembled with the load sensing staple cartridge,
wherein the one or more load sensors are configured to send the sensed parameter to a processor configured to calculate the tissue thickness based on the sensed parameter and to calculate a recommended staple cartridge type for the clamped tissue based on the calculated tissue thickness.

14. The load sensing staple cartridge of claim 13, wherein the processor is configured to calculate the tissue thickness based on a mechanical load, pressure, stress, strain, or deflection sensed by the one or more load sensors.

15. The load sensing staple cartridge of claim 13, wherein the recommended staple cartridge type for the clamped tissue is displayed to a user of the load sensing staple cartridge on a display.

16. The load sensing staple cartridge of claim 15, wherein the load sensing staple cartridge is connected to the display and a power source via a wired connection.

17. A method of determining staple cartridge selection, the method comprising:
clamping tissue with an end effector comprising a cartridge jaw and an anvil jaw pivotably connected to the cartridge jaw, wherein the cartridge jaw comprises a load sensing cartridge inserted therein;
sensing, by one or more load sensors of the load sensing cartridge, a mechanical load, pressure, stress, strain, or deflection;
calculating, by a processor of the load sensing cartridge, a tissue thickness of the clamped tissue based on the sensed mechanical load, pressure, stress, strain, or deflection; and
displaying, by a visual indicator of the load sensing cartridge, visual feedback based on the tissue thickness calculated by the processor, wherein the visual feedback is indicative of a recommended staple cartridge.

18. The method of claim 17, wherein calculating the tissue thickness comprises correlating the sensed mechanical load, pressure, stress, strain, or deflection to a corresponding tissue thickness, the method further comprising:
   determining the recommended staple cartridge by correlating the calculated tissue thickness to a corresponding staple cartridge.

19. The method of claim 17, wherein displaying the visual feedback comprises illuminating one or more light-emitting diodes (LEDs) disposed in or on the load sensing cartridge.

20. The method of claim 17, further comprising marking, by tissue markers of the load sensing cartridge, the clamped tissue.

* * * * *